United States Patent
Inui et al.

(10) Patent No.: US 10,820,823 B2
(45) Date of Patent: Nov. 3, 2020

(54) EVALUATION OF INHIBITORY CIRCUIT AND USE THEREOF

(71) Applicants: INTER-UNIVERSITY RESEARCH INSTITUTE CORPORATION NATIONAL INSTITUTES OF NATURAL SCIENCES, Mitaka (JP); TOKAI OPTICAL CO., LTD., Okazaki (JP)

(72) Inventors: Koji Inui, Okazaki (JP); Yasuyuki Takeshima, Okazaki (JP); Masaya Suzuki, Okazaki (JP); Naoya Kumagai, Okazaki (JP)

(73) Assignees: INTER-UNIVERSITY RESEARCH INSTITUTE CORPORATION NATIONAL INSTITUTES OF NATURAL SCIENCES, Tokyo (JP); TOKAI OPTICAL CO., LTD., Okazaki (JP)

(*) Notice: Subject to any disclaimer, the term of this patent is extended or adjusted under 35 U.S.C. 154(b) by 0 days.

(21) Appl. No.: 15/737,599

(22) PCT Filed: Jun. 17, 2016

(86) PCT No.: PCT/JP2016/068144
§ 371 (c)(1),
(2) Date: Dec. 18, 2017

(87) PCT Pub. No.: WO2016/204282
PCT Pub. Date: Dec. 22, 2016

(65) Prior Publication Data
US 2018/0168476 A1    Jun. 21, 2018

(30) Foreign Application Priority Data
Jun. 18, 2015    (JP) .................................. 2015-122657

(51) Int. Cl.
A61B 5/0484    (2006.01)
A61B 5/0482    (2006.01)
(Continued)

(52) U.S. Cl.
CPC ........ *A61B 5/04842* (2013.01); *A61B 5/0484* (2013.01); *A61B 5/04845* (2013.01);
(Continued)

(58) Field of Classification Search
None
See application file for complete search history.

(56) References Cited

U.S. PATENT DOCUMENTS

| | | |
|---|---|---|
| 2013/0131543 A1 | 5/2013 | Turner et al. |
| 2014/0296945 A1 | 10/2014 | Kato |
| 2015/0133811 A1 | 5/2015 | Suzuki et al. |

FOREIGN PATENT DOCUMENTS

| | | |
|---|---|---|
| EP | 2856929 A1 | 4/2015 |
| JP | H04-347168 A | 12/1992 |

(Continued)

OTHER PUBLICATIONS

Inui et al. Prepulse inhibition of auditory change-related cortical responses. BMC Neuroscience 2012, 13:135. (Year: 2012).*

(Continued)

*Primary Examiner* — Etsub D Berhanu
(74) *Attorney, Agent, or Firm* — Oliff PLC

(57) ABSTRACT

A more practical method for evaluating an inhibitory circuit applicable to a living body, and the use thereof. Herein the action of an inhibitory circuit on an excitatory circuit is evaluated on the basis of attenuation of the brain activity produced by activation of an excitatory circuit by the input of an inhibitory circuit by performing a step for inputting an inhibitory circuit by applying a second trigger in advance of (Continued)

a first trigger to an excitatory circuit activated by a first trigger which is a stimulus or challenge.

19 Claims, 13 Drawing Sheets

(51) Int. Cl.
　　　*A61B 5/05*　　　(2006.01)
　　　*A61B 5/00*　　　(2006.01)
　　　*A61B 5/04*　　　(2006.01)
(52) U.S. Cl.
　　　CPC .............. *A61B 5/05* (2013.01); *A61B 5/4064* (2013.01); *A61B 5/7282* (2013.01); *A61B 5/04001* (2013.01)

(56) References Cited

FOREIGN PATENT DOCUMENTS

| | | |
|---|---|---|
| JP | H08-150210 A | 6/1996 |
| JP | 2004-532475 A | 10/2004 |
| JP | 2006-263113 A | 10/2006 |
| JP | 2008-542328 A | 11/2008 |
| JP | 2009-155341 A | 7/2009 |
| JP | 2011-149478 A | 8/2011 |
| JP | 2013-011877 A | 1/2013 |
| JP | 2012-533309 A | 12/2017 |
| WO | 2002/093318 A2 | 11/2002 |
| WO | 2006059430 | 6/2006 |
| WO | 2006/128802 A2 | 12/2006 |
| WO | 2011/009107 A2 | 1/2011 |
| WO | 2013/061597 A1 | 5/2013 |
| WO | 2014/075029 A1 | 5/2014 |
| WO | 2014/152110 A1 | 9/2014 |

OTHER PUBLICATIONS

Inui et al. Prepulse inhibition of change-related P50m no correlation with P50m gating. SpringerPlus 2013, 2:588. (Year: 2013).*
Braff et al. Human studies of prepulse inhibition of startle: normal subjects, patient groups, and pharmacological studies. Psychopharmacology (2001) 156:234-258. (Year: 2001).*
Huttunen et al. Modulation of somatosensory evoked fields from SI and SII by acute GABAA-agonism and paired-pulse stimulation. NeuroImage 40 (2008) 427-434. (Year: 2008).*
Lenz eta l. Bilateral somatosensory cortex disinhibition in complex regional pain syndrome type I. Neurology 2011;77:1096-1101. (Year: 2011).*
Hoffken et al. Multichannel SEP-recording after paired median nerve stimulation suggests origin of paired-pulse inhibition rostral of the brainstem. Neuroscience Letters 468 (2010) 308-311. (Year: 2010).*
Sep. 6, 2017 International Search Report issued in International Patent Application No. PCT/JP2016/068144.
Sep. 6, 2016 Written Opinion issued in International Patent Application No. PCT/JP2016/068144.
Irahara; "Neuroscientific Research on Mechanisms of Neurotoxicity and Psychosis of Dependent and Unregulated drugs;" The Journal of Pediatric Practice; Aug. 1, 2012; vol. 75; pp. 1436-1442.
Yamada et al.; Project by Health and Labor Sciences Resarch Grant (Regulatory Science Comprehensive Research Promootion Project for Pharmaceuticals, Medical Equipment); 2006; pp. 228-239.
Arai et al.; "Role for the pallidotegmental GABAergic neurons in the impairment of prepulse inhibition of the acoustic startle reflex in animal models of schizophrenia;" Laboratory of Neuropsychopharmacology, Kanazawa University Graduate School of Natural Science and Technology; Sep. 1, 2007; vol. 127; 123-125.
Nakagawa et al.; "Inhibition of somatosensory-evoked cortical responses by a weak leading stimulus;" NeuroImage; 2014; vol. 101; pp. 416-424.
Nakagawa et al.; The 49th Anniversary Congress of Japanese Physcial Therapy Association [online], Japanese Physical Therapy Association; May 30, 2014.
Nakagawa et al.; 50th Anniversary Congress of Japanese Physical Therapy Association [online]; Japanese Physical Therapy Association; Jun. 7, 2015.
Chao et al.; "GABAergic dysfunction mediates autism-like stereotypies and Rett syndrome phenotypes;" Nature; Nov. 11, 2010; 468(7321); pp. 263-269.
Kujirai et al.; "Corticocortical Inhibition in Human Motor Cortex;" Journal of Physiology (London); 1993; 471; pp. 501-519.
May 9, 2017 Office Action issued in Japanese Patent Application No. 2016-575977.
Oct. 3, 2017 Office Action issued in Japanese Patent Application No. 2016-575977.
Nov. 25, 2019 Office Action issued in European Patent Application No. 16811756.2.
Sep. 9, 2019 Office Action issued in Australian Patent Application No. 2016/279532.
Mar. 4, 2020 Office Action issued in Chinese Patent Application No. 201680035466.2.
Graham, "Presidential Address, 1974, The More or Less Startling Effects of Weak Prestimulation," Psychophysiology, vol. 12, No. 3, pp. 238-248.
Stuart et al., "Effects of aging on vibration detection thresholds at various body regions," BMC Geriatrics, vol. 3, 2003, pp. 1-10.
Wiesmann et al., "Functional Magnetic Resonance Imaging of Human Olfaction," Neuroimaging Clinics of North America, vol. 11, No. 2, May 2001, pp. 237-250.
Kobayakawa et al., "Spatio-temporal Analysis of Cortical Activity Evoked by Gustatory Stimulation in Humans," Chem. Senses, vol. 24, 1999, pp. 201-209.
Nguyen et al., "Face representation in the human primary somatosensory cortex," Neuroscience Research, vol. 50, 2004, pp. 227-232.
Chen et al., "Contact heat evoked potentials as a valid means to study nociceptive pathways in human subjects," Neuroscience Letters, vol. 316, 2001, pp. 79-82.
Jan. 29, 2019 Search Report issued in European Patent Application No. 16811756.2.
Zhen, Ni et al.; "Direct demonstration of inhibitory interactions between long interval intracortical inhibition and short interval intracortical inhibition: Descending wave," The Journal of Physiology, vol. 589, No. 12, Jun. 15, 2011, pp. 2955-2962.
Goto, Sae et al.; "Disinhibitory shift of recovery curve of somatosensory-evoked response in elderly: A magnetoencephalographic study," Clinical Neurophysiology, Elsevier Science, IE, vol. 126, No. 6, Sep. 28, 2014, pp. 1228-1233.
Huttunen, J. et al.; "Modulation of somatosensory evoked fields from SI and SII by acute GABA" A-agonism and paired-pulse stimulation; Neuroimage, Elsevier, Amsterdam, NL, vol. 40, No. 2, Apr. 1, 2008, pp. 427-434.
Minoru, Hoshiyama et al.; "Two evoked responses with different recovery functions in the primary somatosensory cortex in humans"; Clinical Neurophysiology, vol. 112, No. 7, Jul. 1, 2001, pp. 1334-1342.
Jan. 29, 2019 Office Action issued in Australian Patent Application No. 2016279532.

* cited by examiner

Test Stimulus

Preceding Stimulus +  Test Stimulus
Test Stimulus

Preceding Stimulus

30ms and 60ms in Advance of the Test Stimulus

EVALUATION OF INHIBITORY CIRCUIT AND USE THEREOF

TECHNICAL FIELD

CROSS-REFERENCE OF RELATED APPLICATION

This application is a related application of Japanese Patent Application No. 2015-122657 filed on Jun. 18, 2015 and claims priority based on this application the contents of which is incorporated herein by reference in its entirety.

The present disclosure relates to evaluation of an inhibitory circuit and the use thereof.

BACKGROUND ART

Neural circuits in the brain and the like consist of pyramidal neurons that transmit excitement and interneurons that inhibit the transmission. It is well known that inhibitory interneurons are mainly GABAergic neurons that use GABA (γ-aminobutyric acid) as a neurotransmitter, and are considered as such also in humans. in animal experiments, the activity of GABAergic neurons is generally observed electrophysiologically or pharmacologically by using brain slice specimens.

Some abnormalities of inhibitory circuits including GABAergic inhibitory interneurons are presumed in many diseases, and examples thereof include epilepsy, essential tremor, schizophrenia, panic, hyperactivity, mania, depression, and autism. It is very important to elucidate the functions of inhibitory circuits and elucidate the pathophysiology of various diseases related to abnormality of brain inhibitory circuits, and also to develop therapeutic drugs for these diseases and understand functional abnormality of inhibitory circuits in individual cases. Further, even when the function of the inhibitory circuit is in a normal range, there are individual differences as to how strongly the inhibitory circuit acts on an excitatory circuit formed by pyramidal neurons transmitting excitation. Since individual differences between the inhibitory circuits are considered to be related to sensory characteristics of individuals, the significance of evaluating inhibitory circuits including inhibitory interneurons is high also when, for example, providing industrial products tailored to the individual customers.

Inhibitory circuits mainly release inhibitory neurotransmitters from the inhibitory interneurons that synaptically connect to an excitatory circuit, and this action can be observed by directly recording an inhibitory postsynaptic potential (IPSP) from within a nerve cell which is the connection target.

Evaluation of such inhibitory circuits is generally performed electrophysiologically or pharmacologically using slice specimens of the brain. Further, since such an evaluation cannot be performed in living animals such as humans, a method in which excitatory activity is taken as an indicator and inhibition occurring therein is observed, instead of directly observing IPSP, has been reported (Non Patent Literature 1). In this method, muscle activity is evoked by applying a magnetic stimulus to a motor cortex, applying a weak magnetic stimulus in advance of this stimulus, and using a phenomenon (prepulse inhibition) that the muscle activity is reduced by preceding stimulus. Then, a degree of inhibition can be evaluated from the reduced muscle activity.

SUMMARY

However, none of the conventional methods directly evaluates the inhibitory circuit using brain activity evoked by stimulus as an indicator, and various problems are associated with these methods. Thus, in animal experiments using brain slice specimens, it is possible only to record the activity of one nerve cell or several nerve cells at most at the same time, and the role played by inhibitory interneurons within the entire specific neural circuit composed of many complex neural networks cannot be evaluated. Further, since slice specimens are used, it is impossible to input a natural stimulus such as a sensory input, and it is impossible to directly evaluate the function of the circuit in the living body. Meanwhile, there are no methods for observing the behavior of inhibitory interneurons in living bodies in humans, and it is very difficult to apply the conventional methods even to animals other than humans.

Furthermore, in the indirect evaluation method using muscle activity as an indicator, this method being described in Non Patent Literature 1, since inhibition can occur at any location of the periphery, spinal cord, and cerebrum, it is impossible to identify whether the detected inhibition is in the inhibitory circuit of the brain. Further, this method cannot be used for individuals with certain diseases including epilepsy due to adverse events of magnetic stimulus. Yet another problem is that the method cannot be used for laboratory small animals such as rats due to the limit of spatial resolution of magnetic stimulus.

It follows from the above that a practical method for evaluating an inhibitory circuit that can be applied to a living body more widely and easily is presently desired. That is, it is desirable to establish a method capable of directly evaluating an inhibitory circuit by using brain activity as an indicator in application to a living body. It is also desirable to establish a method that can. evaluate an inhibitory circuit which is input to various excitatory circuits. it is further desirable to establish a method for industrially using the evaluation results of such inhibitory circuit.

In view of such current circumstances, the present disclosure provides more practical evaluation of an inhibitory circuit applicable to a living body, and the use thereof.

The inventors of the present invention have found that an inhibitory circuit can be input to an excitatory circuit in which brain activity is to be activated by applying a stimulus or the like to a living body. Further, it was found that the degree of attenuation of brain activity caused by the inhibitory circuit can be detected by electroencephalogram, magnetoencephalogram or the like. Thus, the inventors of the present invention have found that the function of an inhibitory circuit in a living body can be directly evaluated by using brain activity as an indicator. According to the present disclosure, the following means are provided.

(1) A system for detecting an inhibitory circuit of a brain, the system comprising:
a detection device that detects a brain activity;
a trigger output device that applies a first trigger that is a stimulus or a task for a living body, and a second trigger that can change a first brain activity induced by an input of the first trigger;
means for acquiring first brain activity information on the first brain activity;
means for acquiring second brain activity information on a second brain activity induced by the application of the first trigger which is accompanied by the application of the second trigger; and.
means for detecting a response in the first brain activity induced by the application of the second trigger on the basis of the first brain activity information and the second brain activity information, wherein the detection system detects the inhibitory circuit of the brain on the basis of the response of the brain activity.

(2) The system according to (1), further comprising means for executing output processing of information on the inhibitory circuit.

(3) The system according to (1) or (2), wherein the first brain activity information is information on a response circuit for a change in the trigger.

(4) The system according to any one of (1) to (3), wherein the first brain activity information is information on a response circuit related to one or two or more selected from the group consisting of a sense of touch, a sense of temperature, a sense of pain and deep sensibility, which are somatic sensations, a sense of vision, a sense of hearing, a sense of taste, and a sense of smell.

(5) The system according to any one of (1) to (4), wherein the first brain activity inforrmration is information on an excitatory circuit.

(6) The system according to any one of (1) to (5), wherein the first brain activity information is information on a response circuit related to a sense of hearing.

(7) The system according to (6), wherein the first brain activity information is information on a response circuit for a sound pressure change.

(8) The system according to any one of (1) to (7), wherein the inhibitory circuit is one or both of a GABA-A mediating inhibitory circuit and a GABA-B mediating inhibitory circuit.

(9) The system according to any one of (1) to (8), wherein the application of the second trigger is implemented in a range of 1 ms or more and 5000 ms or less in advance of the application of the first trigger.

(10) The system according to any one of (1) to (9), wherein the application of the second trigger is implemented in any one or both of a range of 5 ms or more and 60 ms or less and a range of 500 ms or more and 700 ms or less in advance of the application of the first trigger.

(11) The system according to any one of (1) to (10), further comprising means for evaluating an action of the inhibitory circuit on the basis of the first brain activity intbrmation and the second. brain activity information.

(12) The system according to any one of (1) to (11), wherein the detection device detects the brain activity by electrical activity based on brain activity.

(13) The system according to any one of (1) to (12), wherein the detection device detects the brain activity by using an electroencephalogram or a magnetoencephalogram.

(14) The system according to any one of (1) to (13), wherein the second trigger is a trigger with an intensity lower than that of the first trigger.

(15) The system according to any one of (1) to (14), wherein the response of the brain activity is an attenuation of the brain activity.

(16) A method for actuating a detection system for an inhibitory circuit of a brain, the detection system including: a detection device that detects a brain activity; and a trigger output device that applies, to a living body, a first trigger that is a stimulus or a task for the living body, and a second trigger that can change a first brain activity induced by the application of the first trigger;
the method comprising:
acquiring first brain activity information on the first brain activity;

acquiring second brain activity information on a second brain activity induced by the application of the first trigger which is accompanied by the application of the second trigger; and
detecting a response in the first brain activity induced by the application of the second. trigger on the basis of the first brain activity information and the second brain activity information,
wherein the detection systemdetects the inhibitory circuit of the brainn the basis of the response of the brain activity.

(17) A method for analyzing an inhibitory circuit of a brain, the method comprising:
applying, to a subject, a first trigger that is a stimulus or a task for a living body, accompanied by a second trigger that can change a first brain activity induced by the application of the first trigger;
acquiring second brain activity information on a second brain activity induced by the application of the first trigger which is accompanied by the application of the second trigger; and
acquiring a response in the first brain activity induced by the application of the second trigger on the basis of first brain activity information on the first brain activity and the second brain activity information,

(18) A method for examining a disease related to an inhibitory circuit, comprising:
applying, to a subject, a first trigger that is a stimulus or a task for a living body, accompanied by a second trigger that can change a first brain activity induced by the application of the first trigger,
the inhibitory circuit is evaluated on the basis of a response in the first brain activity induced by the application of the second trigger.

(19) A method for evaluating a drug to be used for a disease related to an inhibitory circuit, the method comprising:
applying, to a subject to whom the drug has not been administered, a first trigger that is a stimulus or a task for a living body, accompanied by a second trigger that can change a first brain activity induced by the application of the first trigger; and
applying, to a subject to whom the drug has been administered, a first trigger that is a stimulus or a task for a living body, accompanied by a second trigger that can change a first brain activity induced by the application of the first trigger,
an efficacy of the drug is evaluated on the basis of a response in the first brain activity induced by the application of the second trigger in the subject to whom the drug has not been administered and the subject to whom the drug has been administered.

(20) A screening method for a drug to be used for a disease related to an inhibitory circuit, the method comprising:
applying, to a subject to whom the drug has not been administered, a first trigger that is a stimulus or a task for a living body, accompanied by a second trigger that can change a first brain activity induced by the application of the first trigger; and
applying, to a subject to whom the drug has been administered, a first trigger that is a stimulus or a task for a living body, accompanied by a second trigger that can change a first brain activity induced by the application of the first trigger,
wherein the drug is screened on the basis of a response in each of the first brain activity induced by the application of the second trigger in the subject to whom the drug has not been administered and the subject to whom the drug has been administered.

(21) A system for selecting a drug candidate to be used for a disease related to an inhibitory circuit, the system comprising:

a detection device that detects a brain activity;

a trigger output device that applies a first trigger that is a stimulus or a task for a living body, and a second trigger that can change a first brain activity induced by the application of the first trigger;

means for acquiring first brain activity information on the first brain activity;

means for acquiring second brain activity information on a second brain activity induced by the application of the first trigger which is accompanied by the application of the second trigger;

means for acquiring a response in the first brain activity induced by the application of the second trigger on the basis of the first brain activity information and the second brain activity information; and means for acquiring an inhibitory circuit characteristic of a subject on the basis of the response of the brain activity, wherein a drug candidate to be applied to the subject is selected on the basis of e inhibitory circuit characteristic,

(22) A method for selecting a dmg candidate to be used or a disease related to an inhibitory circuit, the method comprising:

acquiring second brain activity information on a second brain activity obtained by applying, to a subject, a first trigger that is a stimulus or a task for a living body, accompanied by a second trigger that can change a first brain activity induced by the application of the first trigger;

acquiring a response in the first brain activity induced by the application of the second trigger on the basis of first brain activity information on the first brain activity and the second brain activity information; and acquiring an inhibitory circuit characteristic of the subject on the basis of the response of the brain activity, wherein a drug candidate to be applied to the subject is selected on the basis et the inhibitory circuit characteristic.

(23) A method for producing a product that uses a characteristic of an inhibitory circuit, the method comprising:

acquiring second brain activity information on a second brain activity obtained by applying, to a subject, a first trigger that is a stimulus or a task for a living body, accompanied by a second trigger that can change a first brain activity induced by the application of the first trigger;

acquiring a response in the first brain activity induced by the application of the second trigger on the basis of first brain activity information on the first brain activity and the second brain activity information; and acquiring an inhibitory circuit characteristic of the subject on the basis of the response of the brain activity, wherein a product has a function that can adapt to, improve, mitigate or enhancethe inhibitory circuit characteristic being produced on the basis of the inhibitory circuit characteristic.

(24) The method according to (23), wherein the product is a product related to a. human sensory action.

(25) The method according to (23) or (24), wherein the product is a product having a sensory action of adapting, improving, mitigating or enhancing the inhibitory circuit characteristic related to a sense of vision of the subject.

(26) A system for producing a product that uses a characteristic of an inhibitory circuit, the system comprising:

a detection device that detects a brain activity;

a trigger output device that applies a first trigger that is a stimulus or a task for a living body, and a second trigger that can change a first brain activity induced by the application of the first trigger;

means for acquiring first brain activity information on the first brain activity;

means for acquiring second brain activity information on a second brain activity induced by the application of the first trigger which is accompanied by the application of the second trigger;

means for acquiring a response in the first brain activity induced by the application of the second trigger on the basis of the first brain activity information and the second brain activity information; and means for acquiring an inhibitory circuit characteristic of a subject on the basis of the response of the brain activity, wherein a product has a function that can adapt to, improve, mitigate or enhance the inhibitory circuit characteristic being produced on the basis of the inhibitory circuit characteristic.

(27) A method for producing a spectacle lens that uses a characteristic of an inhibitory circuit, the method comprising:

acquiring second brain activity information on a second brain activity obtained by applying, to a subject, a first trigger that is a stimulus or a task for a living body, accompanied by a second trigger that can change a first brain activity induced by the application of the first trigger;

acquiring a response in the first brain activity induced by the application of the second trigger on the basis of first brain activity information on the first brain activity and the second brain activity information; and acquiring an inhibitory circuit characteristic of the subject on the basis of the response of the brain activity, wherein a product has a function that can adapt, improve, mitigate or enhance the inhibitory circuit characteristic being produced on the basis of the inhibitory circuit characteristic.

EMBODIMENTS

Figure 1A:
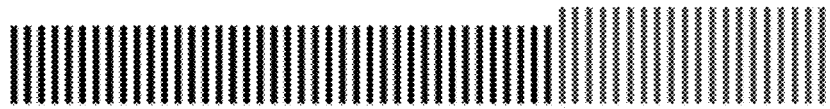
FIG. 1A is a diagram showing a stimulus application pattern for evaluating an inhibitory circuit in a first embodiment.
Figure 1A:
Figure 1A:
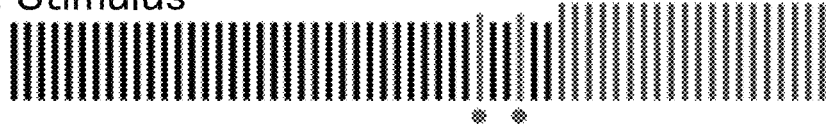
Figure 1A:
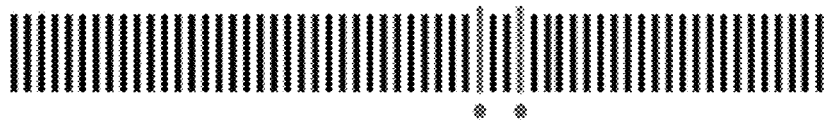

The present disclosure relates to an evaluation method for an inhibitory circuit and the use thereof.

A phenomenon in which brain activity induced by an excitatory circuit activated by stimulus is attenuated by a preceding weak stimulus has been reported by the inventors of the present invention. However, a mechanism causing such attenuation has not been clarified, and there are no reports relating thereto. Therefore, because the mechanism of the phenomenon in. which brain activity induced by the excitatory circuit is attenuated by a preceding weak stimulus has not been clarified, how the measurement results should be used has not been established and it has been difficult for these to be industrially applied.

The attenuation of the excitatory circuit can be generally assumed to be governed by a mechanism realized without mediation of the inhibitory circuit, such as a refractory period of nerve cells, fatigue of nerve terminals, lack of preparation or release of neurotransmitters, and also response attenuation occurring in excitatory synapses, and a mechanism mediated by the inhibitory circuit.

The inventors of the present invention were the first to find that the attenuation phenomenon of brain activity caused by a preceding stimulus is mediated by an inhibitory cell, that is, caused by input of an inhibitory circuit. Furthermore, the inventors of the present invention were the first to find that such a preceding stimulus not only attenuates brain activity but also changes brain activity by the input of the inhibitory circuit.

As described above, the present disclosure is based on a discovery that the phenomenon in which brain activity induced by the excitatory circuit activated by applying a stimulus or the like to a living body is attenuated by a weak stimulus preceding the applied stimulus is generated through mediation of an inhibitory mediating cell (inhibitory circuit). Thus, the disclosure is based on the first confirmation of a phenomenon in which a response of the excitatory circuit in the brain is attenuated due to involvement of the inhibitory circuit. Furthermore, the disclosure is also based on the discovery that brain activity caused by such a preceding stimulus changes through the mediation of the inhibitory mediating cell (inhibitory circuit). The present disclosure provides a method for evaluating an action of an inhibitory circuit on an excitatory circuit, and the use of the method.

As described above, it has already been understood that almost identical inhibitory postsynaptic potential (IPSP) corresponding to the early inhibition obtained in slice specimens of the brain is observed regardless of a type of a mammal, including a human (McCormic, Journal of Neurophysiology, 1989, 62:1018-4027, in particular, p. 1025, right column) and regardless of a location in the brain (Conners et al., Journal of Physiology (1988), 406, pp. 443-468, in particular, p. 462). It has been shown that inhibition by Martinotti cells, which is the greatest candidate for late inhibition, is a mechanism common to neocortex including whole sensory cortex (Packer and Yuste, J. Neurosci. 31 (37); 13260-13271, 2011, in particular, pp. 12-13).

As follows from the above, it is conceivable that a change including the attenuation of brain activity caused by an input of the inhibitory circuit to the excitatory circuit, which is obtained in the present disclosure, reflects a basic excitement inhibiting ability of the individual.

In the present description, "living body" or "subject" means an. animal having an excitatory neural circuit and an inhibitory neural circuit as a neural circuit. Typically, the animal is a mammal, including a human. Preferably, the animal is a human. Further, in addition to humans, various experimental animals and disease model animals such as monkeys, dogs, cats, mice, and rats may be advantageously used in a method for evaluating the inhibitory circuit, a method for evaluating a drug, and a method for screening a drug.

In the present description, "inhibitory circuit" means an inhibitory neural circuit. The "inhibitory circuit" constitutes a neural circuit together with an "excitatory circuit" to be described later. Inhibitory circuits include inhibitory intemeurons (inhibitory neural cells or inhibitory presynaptic cells) and glial cells having an inhibitory function similar to that of mediating cells, and may include inhibitory synaptic and postsynaptic cells. The inhibitory intemeurons generally are GABAergic and include GABA-A-ergic inhibitory intemeurons connected to pyramidal neurons with GABA-A receptors on the cell surface, and GABA-B-ergic inhibitory interneurons targeting pyramidal neurons with GABA-B receptors on the cell surface. Inhibitory circuits are generally distributed in a central nervous system including a cerebral cortex.

In the present description, "excitatory circuit" means an excitatory neural circuit. The excitatory circuits include excitatory pyramidal neurons (excitatory neural cells or excitatory pre-synaptic cells) and may include excitatory synaptic and postsynaptic cells. Excitatory circuits are generally distributed in the central nervous system including the cerebral cortex, in the same manner as the inhibitory circuits.

In the present description, "stimulus or task" refers to all stimuli or tasks to which the subject living body can respond, react and the like. Stimuli in an entire sensory system of a living body may be an object, examples thereof including a sense of touch, a sense of temperature, a sense of pain and deep sensibility, which are somatic sensations, a sense of vision, a sense of hearing, a sense of taste, and a sense of smell. The tasks include those relating to language, thoughts, memories, emotions, recognition, learning, motivation, and exercise. Simple tasks may be exemplified by memory/exercise tasks for quickly responding to a prescribed input, and mental arithmetic tasks.

Hereinafter, representative and non-limiting specific examples of the present disclosure will be described in detail with reference to drawings as appropriate. This detailed description is merely intended to suggest the details for carrying out preferred examples of the present invention to a person skilled in the art and is not intended to limit the scope of the present disclosure, it is also to be understood that the additional features and inventions disclosed hereinbelow may be used separately from or accompanied by other features and inventions to provide a further improved technique for detecting or evaluating an inhibitory circuit.

In addition, the combinations of features and steps disclosed in the following detailed description are not essential in implementing the present disclosure in the broadest sense, and are described in particular only for explaining the representative specific examples of the present disclosure. Further, various features of the representative specific examples described hereinabove and hereinbelow, as well as various features described in the independent and dependent claims, are not intended to be necessarily combined according to the specific examples described herein or in the order listed when providing additional and useful embodiments of the present disclosure.

All the features described in the present description and/or in the claims are intended to be disclosed individually and independently of each other, as a limitation on the disclosure and claimed specific matter of the original application, apart from the configuration of the features described in the embodiments and/or claims. Furthermore, all the descriptions relating to numerical ranges, groups or associations are made with the intention of disclosing the intermediate composition thereof, as a limitation on the disclosure and claimed specific matter of the original application.

Hereinafter, the present disclosure will be described in detail.

(Method for Evaluating or Analyzing an Inhibitory Circuit)

A method for evaluating an inhibitory circuit according to the present disclosure may include inputting an inhibitory circuit to an excitatory circuit, which is to be activated by a first trigger that is a stimulus or a task, by applying a second trigger in advance of the first trigger. In other words, the present evaluation method may include applying, to a subject, a first trigger that is a stimulus or a task for a living body, accompanied by a second trigger that can change a first brain activity induced by the application of the first trigger. The present evaluation method is based on directly grasping a so-called prepulse inhibition phenomenon from a viewpoint of brain activity.

(Excitatory Circuit)

The excitatory circuit to which the present method is applied is not particularly limited. The excitatory circuit is appropriately selected according to the purpose of the present evaluation method, and may be any excitatory circuit which can be activated by a first trigger that is a stimulus or a task and also to which an inhibitory circuit can be input by the application of a second trigger. Such excitatory circuits can be screened as needed. For example, an excitatory circuit suitable for the present evaluation method can he acquired by setting, regarding various triggers, application conditions of the first trigger and the second trigger and observing a response such. as a change of brain activity when the second trigger is used in combination.

As mentioned above, the excitatory circuit is activated by the first trigger which can be various stimuli and tasks, but an excitatory circuit related to stimulus of sensation may be used as the first trigger. The excitatory circuit generally may be exemplified by a response circuit related to a sense of hearing.

Further, a response circuit for a change in the trigger (in particular, a stimulus) may be used as the excitatory circuit A circuit called change-related brain activity may be used as the response circuit for a change in the trigger (Inui et al., BMC Neuroscience 2010, 11:80). A change-related brain activity refers to a brain activity induced by applying certain stimulus or the like while changing the stimulus. Contents of the change in the stimulus are not particularly limited although it depends on the type of stimulus. For example, where the stimulus relates to a sense of hearing, it may be a height (frequency) or an amount (sound pressure) of the sound. The change-related brain activity is relatively little influenced by physical quantity of the stimulus, For example, where sound pressure is considered, a similar activity is recorded when the sound pressure is increased as an example and when the sound pressure is decreased. Therefore, it is preferable to use change-related brain activity as an excitatory circuit. for evaluating an inhibitory circuit.

As has already been described above, the first trigger that is a stimulus or a task may be one or two or more selected from various stimuli of a sense of touch, a sense of temperature, a sense of pain and deep sensibility, which are somatic sensations, a sense of vision, a sense of hearing, a sense of taste, and a sense of smell and various tasks such as memory/ exercise tasks and mental arithmetic tasks.

Any first trigger may be used, as long as it can effectively activate the excitatory circuit and induce brain activity (first brain activity). Generally, the first trigger is appropriately set so that a response phenomenon such as a change phenomenon of brain activity can be observed by the below-described second trigger. For example, the first trigger can be appropriately set so as to observe the attenuation phenomenon of brain activity. When the first trigger is a stimulus, contents of the stimulus, an intensity of the stimulus, and a change mode thereof (for example, when an auditory stimulus is used as the first trigger, the sound volume (sound pressure) or pitch (frequency) thereof) are appropriately selected.

For example, the response circuit for a sound pressuure change is extremely stable and advantageous as an excitatory circuit to be used in the present evaluation method. For example, with the response circuit for a sound pressure change as the above-described change-related brain activity by Tnui et al., a remarkable brain response occurs when a certain sound pressure (for example, about 70 dB) is continuously applied (for example, continuously at appropriate intervals with a length of 1 ins) as a background sound, and suddenly a slight increase in sound pressure (for example, about 10 dB) is generated. This increase in sound pressure corresponds to the first trigger in the present evaluation method.

(Inhibitory Circuit)

In the present evaluation method, an inhibitory circuit is input to the excitatory circuit by applying a second trigger in advance of the first trigger. Any second trigger may be used as long as there is a possibility of changing the excitatory circuit, which is to be induced by the first trigger, by inputting the inhibitory circuit. In relation to the first trigger, the second trigger may be a homologous stimulus or task, or may be a stimulus or task which is not homologous, but is related to the first trigger.

A second trigger homologous or related to the first trigger is a stimulus or a task "homologous" to the first trigger that is a stimulus or a task, or a stimulus or a task "related" to the first trigger. A trigger "homologous" to the first trigger refers to a stimulus or a task identical in type and contents to the stimulus or task which is the first trigger. The identity of the type of the stimulus or task can be based on general classification of stimuli (a sense of touch, a sense of temperature, a sense of pain and deep sensibility, which are somatic sensations, a sense of vision, a sense of hearing, a sense of taste, and a sense of smell) and classification of tasks (memory exercise tasks and mental arithmetic tasks) which have already been explained. Further, the identity of the stimulus or task contents can. be based on the same properties (characteristics) of the stimuli or tasks. Where the properties are the same, a degree (intensity) thereof may be the same or different. For example, when the first trigger is an auditory stimulus of a certain sound pressure, the second trigger homologous to the first trigger is an auditory stimulus related to a sound pressure. Further, it is preferable that the second trigger homologous to the first trigger be changed while remaining homologous to the first trigger. For example, when the first trigger is an auditory stimulus representing a certain change in sound pressure, it is preferable that the second trigger be an auditory stimulus representing a change in sound pressure which is different from the aforementioned change in sound pressure.

A trigger that is "related" to the first trigger is a trigger which may cause a change in the first trigger and which is a stimulus different in type, or a task different in contents from the stimulus or task which is the first trigger. For example, when the first trigger is a visual stimulus that gives a change in contrast, the second trigger related to the first trigger is a visual stimulus that gives a change in luminance. Further, for example, when the first trigger is a visual stimulus created by an image or a video, the second trigger related to the first trigger is an auditory stimulus created by music or sound. In this case, even when the first trigger triggers brain activity relating to a pleasant emotion, and the second trigger triggers a weak unpleasant emotion, it is possible to evaluate an inhibitory circuit for an excitatory circuit which is to be activated by a task triggering a pleasant emotion.

The intensity of the stimulus or task of the second trigger is not particularly limited in relation to the intensity of the stimulus or task of the first trigger. Thus, the intensity of the second trigger may be equal to, higher than, or lower than that of the first trigger. From the viewpoint of making it possible to exclude the possibility of response attenuation caused by the mechanism acting only inside the excitatory circuit, it is preferable that the intensity of the second trigger be lower than the intensity of the first trigge. Further, the intensity of the second trigger may be one which hardly triggers brain activity by itself. The intensity of the second trigger is appropriately set so that an effective change in brain activity (attenuation phenomenon and the like) is revealed.

As for the second trigger, for example, n the above-described response circuit for the sound pressure change of Inui et al., where the sound pressure increase (of the order of 10 dB) causing a remarkable brain response is the first trigger, the sound pressure increase of about 5 dB which is to be applied in advance of the first trigger can he taken as the second trigger.

The second trigger is applied in advance of the first trigger. How much in advance of the first trigger is appropriately set according to the type of the excitatory circuit and the like. An inhibitory circuit to be input to the excitatory circuit, the inhibitory circuit being an evaluation object, can also be selected on the basis of an application timing of the second trigger. For example, a GABA-A mediating inhibitory circuit can be input by applying a second trigger a short time in advance of the first trigger, and a ,GABA-B mediating inhibitory circuit can be input by applying a second trigger a long time in advance of the first trigger, The application of the second trigger, that is, the input of the inhibitory circuit, is not particularly limited, but may be implemented within a range enabling action on the excitatory circuit to be activated by the first trigger. For example, the second trigger can be applied in a range of 5000 ms or less in advance of the application of the first trigger. Further, for example, the second trigger can be applied in a range of 1000 ms or less. This is because where the interstimulus interval in the measurement of brain activity induced by the first trigger exceeds 5000 ms, brain activity induced by the first trigger is unlikely to be affected, and also because various measurement error factors tend to increase. A response phenomenon such as effective attenuation of brain activity can be observed as a result of applying the second trigger in advance of the first trigger within such a time range. Further, the application of the second trigger can be made generally within a range of preferably 1 ms or more, and more preferably about 5 ms or more, in advance of the application of the first trigger.

In particular, for example, a second trigger can be applied in a range of 1 ms or more and 100 ms or less in advance of the first trigger. By applying the second trigger at such a timing, it is possible to input a relatively early inhibitory circuit such as a GABA-A mediating inhibitory circuit formed by basket cells and the like. The range is preferably 10 ms or more and 80 ms or less, more preferably 20 ms or more and 60 ms or less, and still more preferably 30 ms or more and 60 ms or less. These favorable timing differences reflect the remarkable difference in inhibition dynamics depending on the type of GABA receptor and the type of interneurons. Inhibition via GABA-A receptors which is due to basket cells is known to occur most quickly.

It is also considered that the early component can be further classified into two types: inhibition at 20 ms or more and 30 ms or less and inhibition at 40 ms or more and 60 ms or less. The second inhibition observed in normal slice specimens is mediated by GABA-B receptors and is thought to correspond to continuous early inhibition of GABA-A and GABA-B receptors. The timing of this inhibition indicates a peak of inhibition, and recording can be performed even at a timing earlier than the peak. Data can be obtained in units of 1 ms when brain activity is recorded at 1000 Hz, and in units of 0.25 ms when recording at 4000 Hz. Where a stimulus presentation device having a resolution of 1000 Hz or more is used in the presentation of stimuli, the timing of applying the second trigger can be similarly controlled in units of 1 ms. Here, the timing of applying the second trigger in advance is preferably 5 ms or more in consideration of the accuracy of stimulus presentation. It follows from the above the early component is preferably recorded by applying the second trigger in a range of 5 ms or more and 60 ms or less in advance of the first trigger.

Further, for example, the second trigger can be applied in a range of 500 ms or more and 1000 ms or less in advance of the first trigger. By applying the second trigger at such a timing, it is possible to input a relatively late inhibitory circuit formed by Martinotti cells or the like. The range is more preferably 500 ms or more and 750 ms or less, and even more preferably 500 ms or more and 700 ms or less.

As described above, when inputting an inhibitory circuit to a target excitatory circuit, it is possible to identify a preferable timing of applying the second trigger and to input inhibitory circuits of different action mechanisms by applying the second trigger at various timings in a range of 5000 ms or less, more preferably 1000 ms or less, in advance of the first trigger and acquiring a brain activity such as brain waves.

The second trigger may be applied only once or twice or more times. Two or more types of inhibitory circuits may be applied sequentially multiple times in different time spans so that the inhibitory circuits could be evaluated. Further, it is also possible to apply the second trigger continuously two or more times in a single time span, with the intention of, for example, inputting an inhibitory circuit of a certain kind. In the case of applying the second trigger two or more times, a time interval between the second triggers which are to be applied, and a number of times the second triggers are to be applied can also be appropriately set so that an effective response phenomenon of brain activity could be observed.

Concerning the application conditions of the second trigger, the conditions effective for observing the response phenomenon of brain activity can be appropriately selected by applying the second trigger in various modes (that is, the intensity, required time, frequency, number of times, time span and the like) in a range of 1000 ms or less or 800 ms or less in advance of the first trigger. Further, an inhibitory circuit with a distinct operativeness can be also evaluated as a target by identifying operativeness of the response phenomenon of brain activity observed by using a binding agent or the like for GABA-A receptors or GABA-B receptors.

As described above, it is possible to input an inhibitory circuit to an excitatory circuit which is to be activated by the first trigger by applying a second trigger in advance of the first trigger. The input of the inhibitory circuit by the application of the second trigger induces the second brain activity which, for example, has been changed from the first brain activity induced by the excitatory circuit activated by the first trigger. That is, a response in the first brain activity occurs due to the application of the second trigger.

In the present evaluation method, the action of the inhibitory circuit on the excitatory circuit can be evaluated based on the fact that brain activity induced by the activation of the excitatory circuit responds, for example, by changing when the inhibitory circuit is input. Here, the "response" of brain activity is a response in the magnitude (amplitude) of brain activity, such as the presence of intensification or attenuation of the magnitude, the degree thereof, and absence of change. The "response" of brain activity is also a response in the time (latency) in which brain activity occurs, such as the presence of shortening or extension of the tiirie in which the activity occurs, the degree thereof, and absence of change. Further, the "change" in brain activity is a change in the magnitude (amplitude) of brain activity. For example, the magnitude can be intensified or attenuated, and the time (latency) in which brain activity occurs can be shortened or extended. In addition, there are changes (movement) in the location where brain activity occurs. Also, the change in brain activity to be observed may be a change that occurs in periodic activity induced by a first trigger applied in a fixed period.

In the present disclosure, the first brain activity induced by the excitatory circuit activated by the application of the first trigger generates the second brain activity accompanied by a response such as attenuation due to the input of the inhibitory circuit. Therefore, for example, it is possible to observe the response of brain activity caused by the second trigger, that is, the response such as the attenuation of the second brain activity with respect to the first brain activity. The attenuation of brain activity can be measured as a phenomenon in which the magnitude (amplitude) of brain activity decreases. It is also possible to measure the response as a phenomenon in which the time (latency) in which brain activity occurs is delayed. In this manner, the input of the inhibitory circuit in the present disclosure can be detected as a change in magnitude of brain activity, or a change in time in which brain activity occurs. In addition, the "attenuation" of brain activity in the present disclosure is inclusive of not only a decrease in the magnitude of brain activity but also a delay in the time in which brain activity occurs.

Brain activity can be appropriately detected by conventionally known means. Generally, brain activity can be detected by electrical activity based on the activity, change in cerebral blood flow or the like. The electrical activity can typically be detected using electroencephalograms or magnetoencephalograms. Changes in cerebral blood flow can be measured using fMRI (functional Magnetic Resonance imaging) or fNIRS (functional Near-Infrared Spectroscopy), by measuring changes in oxygenated hemoglobin, deoxygenated hemoglobin and the like. Further, if necessary, an imaging device such as CT or NMR can also be used. Here, when evaluating inhibitory circuits with fNIRS or fMRI, it is preferable to perform a preliminary electrophysiological study on which type of inhibition occurs at which timing by using electroencephalograms, magnetoencephalograms or the like, so as to set appropriate first trigger and second trigger.

In the present evaluation method, brain activity can also be detected using a steady-state brain reaction (steady-state response). Steady-state brain responses are usually observed when stimuli are continuously presented at 4 Hz or more, and a sense of visors, a sense of hearing, a somatic sensation, etc. can be measured regardless of sensory organs. In. the case of using a steady-state brain reaction as brain activity, where the analysis-target time of the first trigger is taken as t0 to t1, it is preferable to observe a response such as a change in the steady-state brain reaction in the t0 to t1 range by applying a second trigger in advance of t0. In the present evaluation method, such an arrangement is unrestricted and included in the present disclosure.

Here, supplementary explanation will be given further to the case where, in the present evaluation method, the response of brain activity is detected as, for example, a change in the time in which brain activity occurs. For example, where a stimulus that triggers the above-mentioned steady-state brain reaction is presented, brain activity having a certain rhythm is triggered. Where the stimulus that excites the steady-state brain reaction presented at a certain timing t0 is then changed, a phenomenon can be observed in which the rhythm of brain activity gradually gets faster for a period of about 100 ms to 200 ms from an instant (t0) at which the change took place, and then slows down and returns to the original rhythm. This is "the acceleration of phase" of brain activity and corresponds to brain activity caused by the first trigger in the present invention. By presenting a stimulus which is changed, for example, by a very little time, as a second trigger in advance of t0, it is possible to measure this acceleration of phase as the decrease in the phenomenon (acceleration of phase) that the rhythm observed between from about 100 ms to 200 ms after t0 gradually gets faster, that is, the delay in the time (latency)

in which brain activity occurs. The inhibitory circuit can thus he evaluated also by the change in time in which brain activity occurs, for example.

As described above, in order to detect or evaluate a response such as attenuation of brain activity, the intensity, frequency, required time, number of times, advance time and the like of the second trigger may be appropriately adjusted. Alternatively, a comparison may be made with brain activity of the excitatory circuit activated by the first trigger when the inhibitory circuit is not input. Such a brain activity induced only by the first trigger can be acquired as reference data by separately activating the excitatory circuit due to application of the first trigger, or by activating the excitatory circuit in advance.

In the present evaluation method, in order to evaluate the inhibitory circuit, for example, it is preferable to store the obtained second brain activity information on the second brain activity obtained with the first trigger accompanied by the second trigger, comparing the second brain activity information with information on the first brain activity obtained without the second trigger, and execute the processing of calculating the attenuation rate (%) thereof. Thus, the action (attenuation rate) of the inhibitory circuit can be evaluated on the basis of the information on brain activity (first brain activity information) induced by the activity of the excitatory neural circuit caused by the first trigger, and the information on brain activity (second brain activity information) induced by the activity of the excitatory neural circuit caused by the first trigger accompanied by the second trigger.

Furthermore, in the present evaluation method, it is preferable to acquire information on brain activity (third brain activity information) by applying only the second trigger. This is because when brain activity is induced only by the second trigger, this also needs to be taken into consideration. In this case, it is preferable that information (difference information) obtained by subtracting the third brain activity information from the second brain activity information be taken, in place of the second brain activity information, as the brain activity information to be compared with the first brain activity information.

For such a method, a computer such as a PC having a control means such as a CPU can be used as appropriate, It is also preferable to perform observations on a display (monitor) that displays information on the attenuation rate and also on electroencephalogram and magnetoencephalogram.

According to the above-described evaluation method, functions of an inhibitory circuit in a living body can be evaluated. Such an evaluation of an inhibitory circuit makes it possible to diagnose and examine diseases that may be represented by some abnormality in the inhibitory circuit, such as epilepsy, essential tremor, schizophrenia, panic, hyperactivity, mania, depression, and autism, and evaluate the effects of drugs and the like. In particular, since the effect of the inhibitory circuit on brain activity is directly evaluated, by contrast with the conventional methods, more effective evaluation becomes possible.

Such an evaluation was extremely difficult to perform by the conventional methods, and it is made possible for the first time by this evaluation method. As a result, it is possible not only to detect abnormalities and the like in inhibitory circuits in the conventional diseases and to elucidate the cause of the diseases, but also to clarify therapeutic targets and treatment guidance by identifying diseases related to inhibitory circuits.

In addition, according to the present evaluation method, by applying the present evaluation method to a subject, for example, a specific individual such as a human or a certain group, it is possible to acquire and analyze the characteristics (inhibitory circuit characteristics) of the inhibitory circuits of the individual or the group. The obtained inhibitory circuit characteristics are strongly correlated with the sensory characteristics of animals such as humans. Therefore, based on the inhibitory circuit characteristics of individuals or groups, it becomes possible to select drugs, select treatment, as well as provide products that can reduce inconvenience and improve convenience in daily life. The group can be exemplified by human groups classified by any one or two or more of the sex, age, occupation, lifestyle, physical characteristics (height, weight, BM, disease history, genetic information, blood type, etc.), disease history, drug administration history, and nationality.

(Method for Examining Disease Related to Inhibitory Circuit)

The above-described evaluation method of the present disclosure can be used in a method for examining a disease related to a GABAergic inhibitory circuit of the present disclosure. That is, by using the abovementioned evaluation method to evaluate the action of the inhibitory circuit on the basis of the response in the first brain activity induced by the application of the second trigger, it becomes possible to diagnose such a disease. Since the action (characteristic) of the inhibitory circuit of the subject can be acquired, the disease and the cause of the disease can be identified. For example, in the case where the action of the inhibitory circuit is declining, it is possible to diagnose the symptoms or possibility of the onset of such a disease. In addition, the progress, prognosis, drug effect, therapeutic effect, and healing of such a disease can be diagnosed by a decrease or an increase in the action of the inhibitory circuit. Therefore, the present examination method can also be implemented as a diagnostic method. Conventionally, it has been difficult to examine diseases considered to be related to abnormality of inhibitory circuits such as GABAergic interneurons in living bodies. However, since the action of the inhibitory circuit can be directly evaluated with the present examination method, this method can be used for, for example, accurately diagnosing such diseases or for assisting the diagnosis.

Diseases related to inhibitory circuits, particularly diseases related to GABAergic inhibitory circuits, can be exemplified by epilepsy, essential tremor, schizophrenia, panic, overactivity, mania, depression, and autism.

(Method for Evaluating Drug to Be Used for Disease Related to Inhibitory Circuit)

The present evaluation method may include inputting an inhibitory circuit to an excitatory circuit, which is to be activated by a first trigger that is a stimulus or a task for a living body to which the drug has been administered, by applying a second trigger in advance of the first trigger; and inputting an inhibitory circuit to an excitatory circuit, which is to be activated by a first trigger that is a stimulus or a task for a living body to which the drug has not been administered, by applying a second trigger in advance of the first trigger. According to the aboveidescribed method it is possible to evaluate the efficacy of the drug on the basis of the generation of the second brain activity, which is a response such as a change due to the input of the inhibitory circuit, by the first brain activity induced by the activation of the excitatory circuit in the living body to which the drug has been administered and the living body to which the drug has not been administered.

In other words, the present evaluation method includes applying, to a subject to whom the drug has not been administered, a first trigger that is a stimulus or a task for a living body, accompanied by a second trigger that can change a first brain activity induced by the application of the first trigger; and applying, to a subject to whom the drug has been administered, a first trigger that is a stimulus or a task for a living body, accompanied by a second trigger that can change a first brain activity induced by the application of the first trigger, the efficacy of the drug being evaluated on the basis of a response in the first brain activity induced by the application of the second trigger in the subject to whom the drug has not been administered and the subject to whom the drug has been administered.

For the above-mentioned elements such as the excitatory circuit, inhibitory circuit, first trigger, first brain activity, and second trigger in the method for evaluating a drug, these various modes of the evaluation method can be applied as they are. Further, the above-mentioned contents can also be applied to diseases related to inhibitory circuits.

Such a method for evaluating a drug is also suitable as a method for selecting a drug to be applied to a living body and a method for monitoring a medicinal effect obtained in the drug applied to a living body.

Conventionally, it has been difficult to properly evaluate drugs for diseases considered to be related to abnormalities of inhibitory circuits such as GABAergic intemeurans in a living body. However, since the action of the inhibitory circuit can be directly evaluated with the present drug evaluation method, the effect of the drug can be accurately evaluated.

(Method for Screening Drug to Be Used for Prevention or Treatment of Disease Related to Inhibitory Circuit)

The present screening method can include inputting an inhibitory circuit to an excitatory circuit, which is to be activated by a first trigger that is a stimulus or a task for a living body to which the drug has been administered, by applying a second trigger in advance of the first trigger; and inputting an inhibitory circuit to an excitatory circuit, which is to be activated by a trigger that is a stimulus or a task for a living body to which the drug has not been administered, by applying a second trigger in advance of the first trigger. With this screening method, it is possible to screen a drug which enhances or reduces the action of the inhibitory circuit on the basis of a response such as a change due to the input of the inhibitory circuit by the brain activity induced by the activation of the excitatory circuit in the living body to which the drug has been administered and the living body to which the drug has not been administered.

In other words, the present screening method includes applying, to a subject to whom the drug has not been administered, a first trigger that is a stimulus or a task for a living body, accompanied by a second trigger that can change a first brain activity induced by the application of the first trigger; and applying, to a subject to whom the drug has been administered, a first trigger that is a stimulus or a task for a living body, accompanied by a second trigger that can change a first brain activity induced by the application of the first trigger, the drug being screened on the basis of a response in the first brain activity induced by the application of the second trigger to the subject to whom the drug has not been administered and the subject to whom the drug has been administered.

For the above-mentioned elements such as the excitatory circuit, inhibitory circuit, first trigger, and second trigger in the method for screening a drug, these various modes of the evaluation method can he applied as they are. Further, the above-mentioned contents can also be applied to diseases related to inhibitory circuits.

Conventionally, it has been difficult to properly evaluate drugs for diseases considered to be related to abnormalities of inhibitory circuits such as GABAergic intemeurons in a living body. However, since the action of the inhibitory circuit can be directly evaluated with the present screening method, the effective drug can be efficiently screened.

(Detection System for inhibitory Circuit)

The detection system for an inhibitory circuit of the present disclosure may include a detection device that detects brain activity, and a device capable of applying to a living body a first trigger that is a stimulus or a task for the living body, and capable of applying a second trigger in advance of the first trigger. With the present system, a response such as a change in the brain activity caused by the application of the second trigger can be detected by acquiring first brain activity information on brain activity induced by the application of the first trigger, and second brain activity information on brain activity induced by the application of the first trigger accompanied by the second trigger.

In other words, the present detection system can have the following configuration. The detection system can include a detection device that detects a brain activity; a trigger output device that applies a first trigger that is a stimulus or a task for a living body, and a second trigger that can change a first brain activity induced by an input of the first trigger; means (first brain activity information acquiring means) for acquiring first brain activity information on the first brain activity; means (second brain activity information acquiring means) for acquiring second brain activity information on a second brain activity induced by the application of the first trigger which is accompanied by the application of the second trigger; and means (brain activity response detecting means) for detecting a response in the first brain activity induced by the application of the second trigger on the basis of the brain activityinformation and the second brain activity information.

In this detection system, brain activity induced by the application of the first trigger is induced by the excitatory circuit activated by the first trigger. In addition, brain activity induced by the application of the first trigger accompanied by the second trigger is generated as a result of attenuating brain activity, which is induced by the activation of the excitatory circuit, by inputting the inhibitory circuit by the application of the second trigger.

A conventionally known device can be used for detecting brain activity. For example, an electroencephalogram, a magnetoencephalogram or an acquisition device such as a fNIRS or a fMRI can be used, If necessary, an imaging device such as a CT or an NMR may be provided, In particular, an electroencephalogram (electroencephalograph) or a magnetoencephalogram (magnetoencephalogaph) is preferable because it can directly detect electrical activity based on brain activity and the like.

The device capable of applying the first trigger and the second trigger to the living body is appropriately selected depending on the first trigger and the second trigger to be used. For example, when an auditory stimulus is used as a trigger, a conventional well-known sound signal generating device can be used. Further, for example, when using a visual stimulus as a trigger, conventional well-known visual stimulus generators such as a display, a projector, and an LED light source can be used.

The first brain activity information acquiring means of the present system acquires an electrical signal or the like based on the first brain activity which has been acquired from the brain activity detection device and stored, if necessary, in a memory or the like, by applying the first trigger, and this electrical signal or the like can be acquired, for example, by computational processing as predetermined brain activity information (for example, brain waves or the like relating to the application of the first trigger) with reference to related information relating to the application of the first trigger, for example, such as the type, intensity, and tinting of the first trigger. Likewise, the second brain activity information acquiring means can acquire an electrical signal or the like based on the second brain activity, which has been acquired from the brain activity detection device by the application of the second trigger and the first trigger, for example, by computational processing as predetermined brain activity information with reference to related information relating to the application of the second trigger.

The brain activity response detecting means of the present system detects the response of brain activity on the basis of the first brain activity information and the second brain activity information. By detecting the response of brain activity, the inhibitory circuit can be evaluated. The detection of the response of brain activity and the evaluation of the inhibitory circuit have already been described. The brain activity response detecting means can calculate the action of the inhibitory circuit (attenuation rate or the like), as has already been described, by computational processing or the like using the first brain activity information and the second brain activity information according to the type or the like of the brain activity information to be processed.

The present system can also include a computer such as a PC equipped with a control means capable of storing and comparing brain activity information and calculating the attenuation rate. The control means may control the evaluation background in the present evaluation method and the like (for example, the application environment of a stimulus or the like before a change in the case of using a change response circuit) or the application timing of the first trigger, and also may control the second trigger so that the second trigger is applied at a specific timing, with a specific frequency, of a specific intensity, and a specific number of times. The first brain activity information acquiring means, the second brain activity information acquiring means, and the brain activity response detecting means of the present system are generally provided as part of the control means of a processor such as a computer.

The present system can also include a display (monitor) and a printer as an output means for outputting (displaying) the detection results on the inhibitory circuit, such as the attenuation rate, as well as information on brain activity recorded in an electroencephalogram, a magnetoencephalogram and the like.

At the same time, such a detection system can be used not only to detect the action of the inhibitory circuit but also as an evaluation system for evaluating the degree of the action and the like.

Figure 10:
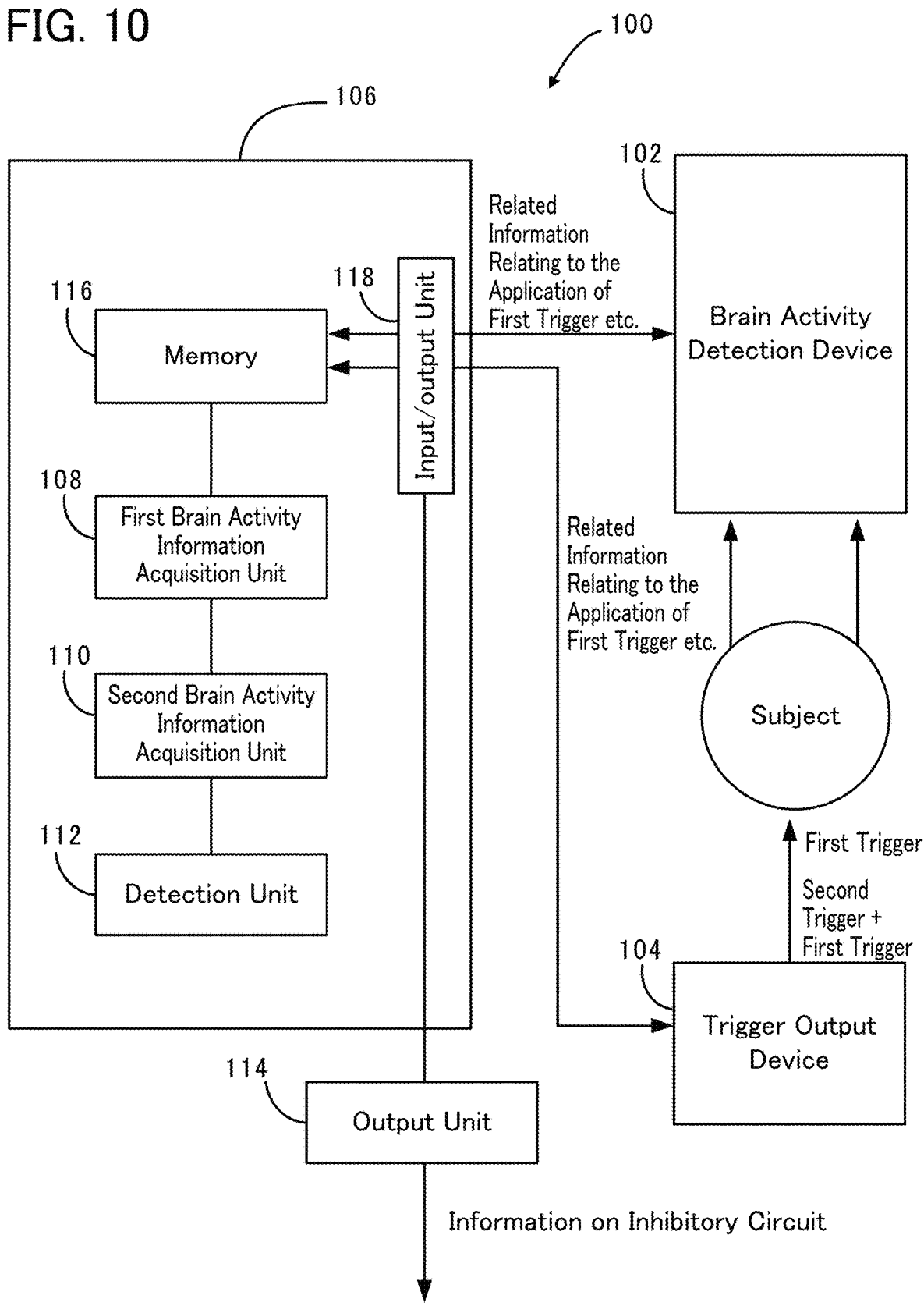
FIG. 10 is a diagram showing an outline of an example of a detectionsystem of an inhibitory circuit.

Here, FIG. 10 is a block diagram of a schematic configuration as an example of the present detection system. A detection system 100 shown in FIG. 10 includes a. brain activity detection device 102, a trigger output device 104, and a processor 106 including a first brain activity information acquisition unit 108 serving as the first brain activity information acquiring means, a second brain activity information acquisition unit 110 serving as the second brain activity acquisition information acquiring means, a detection unit 112 as brain activity response detecting means, and also an output unit 114 as means for executing output processing of information on an inhibitory circuit. The processor 106 is generally configured as a computer or the like having a CPU, and the processor can include an appropriate memory 116 as well as an input/output unit 118 as an input/output interface.

The present detection system 100 shown in FIG. 10 is an example and is not limiting. Various types of detection systems for an inhibitory circuit can be configured by a person skilled in the art on the basis of the disclosure of the present description. For example, the configuration including the output unit 114 is not limiting. For example, in some cases, the brain activity detection device 102 can output brain activity information as is by incorporating an analog circuit or the like. Further, in the present detection system 100, the brain activity detection device 102, the trigger output device 104, and the processor 106 are shown as separate units, but the present invention is not limited to such a configuration, and all those units may be integrated into a single detection device. It is also possible to configure a detection system in which some of these units are integrated.

Figure 11:
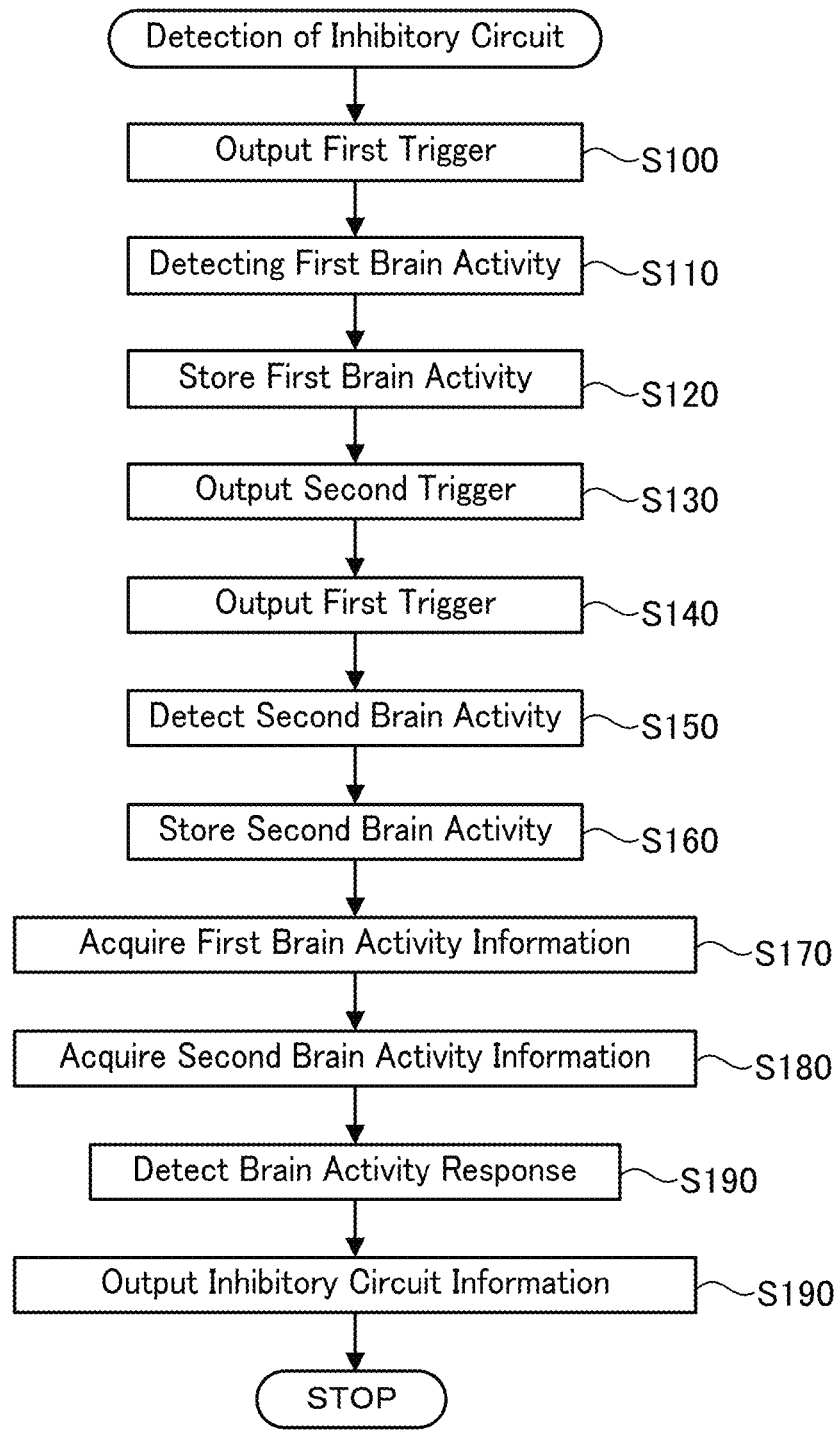
FIG. 11 is a diagram showing an example of a flow for detecting an inhibitory circuit by the detection system for the inhibitory circuit shown in FIG. 10.

An example of the inhibitory circuit detection or evaluation flow in the present detection system 100 shown in FIG. 10 is shown in FIG. 11, and the operation of the present detection system in the method for detecting or evaluating an inhibitory circuit will be described hereinbelow. It should be noted that various types of information and programs for executing the detection of the inhibitory circuit have been stored in advance in a memory 116 of the processor 106 of the present detection system 100, examples thereof including an application program for applying a trigger such as application conditions of the first trigger and application conditions of the second trigger required for detecting the inhibitory circuit, a computational program for calculating the first and second brain activity information by processing electrical signals or the like based on brain activity induced in the subject by these triggers, and a computational program for comparing the first brain activity information with the second brain activity information, detecting the response of the first brain activity caused by the application of the second trigger and calculating the response as the attenuation rate of the first brain activity or the like.

As shown in FIG. 11, firstly, the processor 106 outputs an output signal of the first trigger according to the preset application conditions of the first trigger to the trigger output device 104. The trigger output device 104 outputs (applies) a predetermined first stimulus to the subject (step S100). A tester personnel may manually apply the output signal to the trigger output device 104.

The processor 106 may read the related information on the application of the first trigger and the related information on the application of the second trigger from the memory 116 and appropriately output the information to the brain activity detection device 102 to process the information in the brain activity detection device 102. The related information of this type may be output to the brain activity detection device 102. via the trigger output device 104 or from the trigger output device 104.

The brain activity (first brain activity) occurring in the subject due to the application of the predetermined first trigger to the subject is detected as an electrical signal or the like by the brain activity detection device 102 (step S110). For example, the brain activity detection device 102 performs, as necessary, appropriate processing such as signal amplification and analog filter processing on the detected electrical signal and the like, and outputs the processed signal to the processor 106. The processor 106 stores the output signal in the memory 116 (step S120).

The processor 106 then outputs an output signal of the second trigger according to the preset application conditions of the second trigger to the trigger output device 104. The trigger output device 104 outputs (applies) the predetermined second trigger to the subject (step S130). Furthermore, the processor 106 outputs an output signal of the first trigger relating to the case where the output is accompanied by the application of the preset second trigger to the trigger output device 104, and the trigger output device 104 outputs the predetermined first trigger to the subject (step S140).

As a result of the application of the predetermined second trigger to the subject, the brain activity detection device 102 detects brain activity (second brain activity) occurring in the subject as an electrical signal or the like (step S150). For example, the brain activity detection device 102 performs, as necessary, appropriate processing on the detected electrical signal and the like, and outputs the processed signal to the processor 106. The processor 106 stores the output signal in the memory 116 (step S160).

Next, the first brain activity information acquisition unit 108 uses, for example, a predetermined computational program to process the first brain activity stored in the memory 116 and calculate the first brain activity, for example, as the first brain activity information such as brain waves (step S170). Further, the second brain activity information acquisition unit 110 also calculates the second brain activity information in the same manner (step S180). These types of brain activity information are appropriately stored in the memory 116.

The detection unit 112 reads out the first brain activity information and the second brain activity information by using a predetermined computational program and compares the two types of brain activity information to detect a response in the brain activity induced by the application of the second trigger (step S190). Specifically, the response in brain activity is the response (result) of the first brain activity induced by the second trigger, and more specifically, the change or attenuation such as described above.

For example, the detection unit 112 can detect the inhibitory circuit by calculating such. a change as information related to the evaluation of the inhibitory circuit by computational processing. For example, when the first brain activity is attenuated by the second trigger, the change can be calculated as an inhibition rate (%) of brain activity. The calculation of the inhibition rate itself is well known to a person skilled in the technical field of brain activity evaluation.

Then, the detection result is output to the output unit 114 (step S200). The output contents can be set as appropriate. For example, it can be the first brain activity information, the second brain activity information, and the inhibition rate. The output unit 114 is not particularly limited and may be a general display, printer and the like, and a display unit included in the brain activity detection device 102 may be also used. As described above, with the present detection system, the detection or evaluation of an inhibitory circuit can be performed non-invasively with high accuracy.

(Selection System and Selection Method for Drug Candidate to Be Used for Disease Related to Inhibitory Circuit)

According to the present description, a selection system for a drug candidate to be used for a disease related to an inhibitory circuit is also provided. The present selection system includes a detection device that detects a brain activity; a trigger output device that applies a first trigger that is a stimulus or a task for a living body, and a second trigger that can change a first brain activity induced by the application of the first trigger; means for acquiring first brain activity information on the first brain activity; means for acquiring second brain activity information on a second brain activity induced by the application of the first trigger which is accompanied by the application of the second trigger; means for acquiring a response in the first brain activity induced by the application of the second trigger on the basis of the first brain activity information and the second brain activity information; and means for acquiring an inhibitory circuit characteristic of a subject on the basis of the response of the brain activity, a drug candidate to be applied to the subject being selected on the basis of the inhibitory circuit characteristic. With the present selection system, it is possible to select a drug suitable for, for example, treating a disease related to an inhibitory circuit according to the inhibitory circuit characteristic of the subject. Therefore, economic and physical burden on drug selection can be reduced and subjects can receive appropriate treatment according to their own inhibitory circuit characteristics.

Various modes already described in relation to the present evaluation method can be applied to the brain activity detection device, the output device for the first and second triggers, the first brain activity, the first brain activity information, the second brain activity, the second brain activity information, the response of the brain activity, the detection thereof and the like in the present selection system. Further, examples of the subject in the present selection system include a patient having a disease related to the inhibitory circuit as well as a subject that can have such a disease or a healthy person.

The present selection system may also be implemented as a method for selecting a drug candidate to be used for a disease related to an inhibitory circuit. Thus, according to the present description, the selection method includes: acquiring second brain activity information on a second brain activity obtained by applying, to a subject, a first trigger that is a stimulus or a task fur a living body, accompanied by a second trigger that can change a first brain activity induced by the application of the first trigger; acquiring a response in the first brain activity induced by the application of the second trigger on the basis of first brain activityactivityinformation on the first brain activity and the second brain activity information; and acquiring an inhibitory circuit characteristic of the subject on the basis of the response of the brain activity, a drug candidate to be applied to the subject being selected on the basis of the inhibitory circuit characteristic.

(Production Method and Production System for Product Using Characteristic of Inhibitory Circuit)

According to the present description, there are provided a production method and r production system for a product using the characteristic of an inhibitory circuit. The present production system includes: a detection device that detects a brain Activity; a trigger output device that applies a first trigger that is a stimulus or a task for a living body, and a second trigger that can change a first brain activity induced by the application of the first trigger; means for acquiring first brain activity information on the first brain activity; means for acquiring second brain activity information on a second brain activity induced by the application of the first trigger which is accompanied by the application of the second trigger; means for acquiring a response in the first brain activity induced by the application of the second trigger on the basis of the first brain activity information and the second brain activity information; and means for acquiring an inhibitory circuit characteristic of a subject on the basis of the response of the brain activity. With the present production system, it is possible to produce, on the basis of the inhibitory circuit characteristic, a product having a function that can adapt, improve, mitigate or enhance the inhibitory circuit characteristic.

Further, according to the present description, there is provided a method for producing a product using the characteristic of an inhibitory circuit. The present production method includes acquiring second brain activity information on a second brain activity obtained by applying, to a subject, a first trigger that is a stimulus or a task for a living body, accompanied by a second trigger that can change a first brain activity induced by the application of the first trigger; acquiring a response in the first brain activity induced by the application of the second trigger on the basis of first brain activity information on the first brain activity and the second brain activity information; and acquiring an inhibitory circuit characteristic of the subject on the basis of the response of the brain activity. With the present production method, it is possible to produce, on the basis of the inhibitory circuit characteristic, a product having a function that can adapt, improve, mitigate or enhance the inhibitory circuit characteristic.

Various modes already described in relation to the present evaluation method can be applied to the brain activity detection device, the output device for the first and second triggers, the first brain activity, the first brain activity information, the second brain activity, the second brain activity information, the response of the brain activity, the detection thereof and the like in the present production system and production method. Further, the subject in the present selection system is not particularly limited and can be human or various groups.

With the present production system and production method, it is possible to produce, on the basis of the acquired inhibitory circuit characteristic, a product having a function that can adapt, improve, mitigate or enhance the inhibitory circuit characteristic. Since the inhibitory circuits inhibit the excitatory circuits related to sensory characteristics, inhibitory circuit characteristics are thought to be closely related to sensory characteristics of individuals. Examples of products that can use inhibitory circuit characteristics include products related to sensory actions of humans or the like. Products related to sensory actions are also products related to stimuli or tasks which have already been described. Such products include, but are not limited to, eye-related products such as spectacle lenses and contact lenses, hearing-related products such as hearing aids, headphones and earphones, products related to somatic sensation such as clothing, bedding, and furniture such as sofas and beds, products related to a sense of taste and/or a sense of smell such as foods and drinks, products related to a sense of smell such as fragrances, perfumes, and cosmetics, and mobile bodies such as vehicles in which various sensory actions are combined.

Based on the inhibitory circuit characteristic, it is possible to produce a product using the characteristic of the inhibitory circuit and having a "sensory action" that adapts to, improves, mitigates or enhances the inhibitory circuit characteristic. Examples of the "sensory action" in various products include "visual comfort" of spectacle lenses and contact lenses related to the sense of vision, "hearing comfort" of hearing aids related to the sense of hearing, "wearing comfort" of clothes or "sleeping comfort" of beds related to the somatic sensation, "drinking comfort" and "eating comfort" of foods and drinks related to the sense of taste, and "ride comfort" of vehicles considered to be related to a complex feeling. Therefore, it is possible to predict usability at the time of use of certain products or to adjust or design the product to improve the usability thereof based on the acquired inhibitory circuit characteristics of individuals and groups. A method for producing such a product is particularly meaningful with respect to customized products produced by a built-to-order system, such as tailor-made and custom-made products.

Hereinafter, as an example, a method and a system including ordering and producing of spectacle lenses will be explained with respect to a case in which an inhibitory circuit characteristic of a spectacle lens purchaser is acquired by the method and system disclosed in the present disclosure. First, information on the inhibitory circuit characteristic (for example, inhibition rate) of the spectacle lens purchaser is transmitted, in addition to spectacle lens information such as usual ordering information on spectacle lenses, for example information on eyes of the spectacle lens purchaser (spherical power, astigmatic power, axis, prism power, prism angle and the like) as well as spectacle frame wearing information (forward tilt angle, warp angle, vertex distance, pupillary distance (PD) and the like), spectacle frame information (lens shape, necessary lens diameter, lens curve and the like), and product type and designation of spectacle lenses (product name, monofocal lens, progressive refractive power lens, lens color, coat type and the like), at the time of ordering of the spectacle lens by using communication means such as Internet, telephone, FAX, online ordering and the like from the entity making a spectacle lens order (for example, a spectacle store) to a spectacle lens producer.

Next, the spectacle lens producer reflects the inhibitory circuit characteristic of the spectacle lens purchaser in the process of setting (designing) the product specifications that will reflect the acquired ordering information. For example, when the inhibition rate of the spectacle lens purchaser against the luminance change of the visual stimulus is higher than an average of the inhibition rates of typical subjects, it can be understood that for the spectacle lens purchaser, a luminance change of the degree of a prepulse (corresponding to the second trigger) presented at the time of measurement causes a large input of the inhibitory circuit. In such a case, the spectacle lens purchaser is supposed to have an individual characteristic of being relatively sensitive to glare.

In such a case, the spectacle lens producer, for example, makes the lens color dark, sets the lens color specifications such as to obtain a spectral transmittance waveform in which a cut-off ratio of blue light of about 400 nm to 450 nm is increased, or reduces the transmission in a range of 460 nm to 480 nm, thereby making it possible to produce a product in which a light stimulus to be input to ipRGC (intrinsically photosensitive retinal ganglion cell) is reduced. Further, when a specific personal characteristic is presumed with respect to the sense of vision, a person skilled in the art can appropriately apply various specifications on the lens by using well-known design techniques and production techniques.

Further, for example, the inhibition rate in a case where a prepulse stimulus is presented as a blur of a stimulus image is measured in a spectacle store or by an ophthalmologist, and this inhibition rate (inhibitory circuit characteristic) is transmitted as part of the ordering information to the spectacle lens producer. When the inhibition rate is lower than that of a typical subject, it can be determined that in the spectacle lens purchaser, no inhibitory circuit is input even when a vision is slightly blurred, and conditions of good vision and conditions of slightly blurred vision cannot be distinguished from each other.

In such a case, it is possible to produce and provide to the spectacle lens purchaser a lens with design specifications such that removal of distortion is prioritized over removal of blurring. For example, in order to produce a lens such that distortion is removed in preference to removal of blurring, if the lens to be produced is a monofocal aspherical lens, astigmatism is improved in preference to field curvature, and if the lens to be produced is a progressive refractive power lens, the design can be of an aberration dispersion type.

The spectacle lens produced in this manner by using the information on the inhibitory circuit characteristic is placed in a spectacle lens frame which is purchased separately through a. spectacle shop or the like, fitted to the spectacle lens purchaser, and delivered to the spectacle lens purchaser. By doing as described above, it is possible to produce a spectacle lens by using the inhibitory circuit characteristic.

The above-described setting example of product specifications is only an example and is not limiting. For example, where a response to glare is to be improved, it can be supposed to be necessary to set different product specifications even when the inhibition rate is the same in subjects of good health and subjects with ocular diseases such as age-related macular degeneration, retinal pigment degeneration, and glaucoma. Where the number of retinal photoreceptor cells or optic nerves is decreased due to an ocular disease, the stimulus can be amplified in the living body and information can be transmitted to irritate the brain even when the stimulus amount is the same. Further, the history of disease together with age are also important factors, and since it is assumed that the speed of information transmission from sensory organs to the brain is delayed due to aging, when producing products by using the inhibitory circuits, it is also preferable to consider the age of the purchaser.

Although various embodiments have been described in connection to the present disclosure, the present evaluation method, the method for examining or diagnosing a disease related to a GABAergic inhibitory circuit, the method for evaluating a drug to be used for the prevention or treatment of the disease, the method for screening the drug, and the method for monitoring the drug may include an action step of applying a stimulus or the like to a human body. However, these methods can be implemented as the actuation methods of the abovementioned detection system or evaluation system for an inhibitory circuit and also can be implemented as methods for acquiring information on the brain activity obtained by applying stimulus or the like to the human body, and evaluating the action of an inhibitory circuit by using this information. Accordingly, the present description can include the following modes.

(Clause 1) A method for evaluating an inhibitory circuit, the method comprising:

inputting an inhibitory circuit to an excitatory circuit, which is to be activated by a first trigger that is a stimulus or a task, by applying a second trigger which is lower in intensity than the first trigger in advance of the first trigger, wherein an action of the inhibitory circuit on the excitatory circuit is evaluated on the basis of attenuation caused by the input of the inhibitory circuit in brain activity induced by activation of the excitatory circuit.

(Clause 2) The method according to (Clause 1), further comprising activating the excitatory circuit by applying the first trigger.

(Clause 3) The method according to (Clause 1) or (Clause 2), wherein the excitatory circuit is a response circuit for a change in the trigger.

(Clause 4) The method according to any one of (Clause 1) to (Clause 3), wherein the excitatory circuit is a response circuit related to one or two or more selected from the group consisting of a sense of touch, a sense of temperature, a sense of pain and deep sensibility, which are somatic sensations, a sense of vision, a sense of hearing, a sense of taste, and a sense of smell.

(Clause 5) The method according to any one of (Clause 1) to (Clause 4), wherein the excitatory circuit is a response circuit related to a sense of hearing.

(Clause 6) The method according to (Clause 5), wherein the excitatory circuit is a response circuit for a sound pressure change.

(Clause 7) The method according to any one of (Clause 1) to (Clause 6), wherein the inhibitory circuit is one or both of a GABA-A mediating inhibitory circuit and a GABA-B mediating inhibitory circuit.

(Clause 8) The method according to any one of (Clause 1) to (Clause 7), wherein the input of the inhibitory circuit is implemented in a range of 1000 ms or less in advance of the application of the trigger.

(Clause 9) The method according to any one of (Clause 1) to (Clause 8), wherein the input of the inhibitory circuit is implemented in any one or both of a range of 10 ms or more and 30 ms or less and a range of 500 ms or more and 700 ms or less in advance of the application of the trigger.

(Clause 10) The method according to any one of (Clause 1) to (Clause 9), wherein the action of the inhibitory circuit is evaluated on. the basis of first brain activity information on the brain activity induced by activity of the excitatory circuit nerve circuit caused by the first trigger, and second brain activity information on the brain activity induced by activity of the excitatory circuit nerve circuit caused by the first trigger accompanied by the second trigger.

(Clause 11) The method according to any one of (Clause 1) to (Clause 10), wherein the brain activity is detected by electrical activity based on brain activity.

(Clause 12) The method according to any one of (Clause 1) to (Clause 11), wherein the brain activity is detected by using an electroencephalogram or a magnetoencephalogram, (Clause 13) A method for examining a disease related to an inhibitory circuit, the method comprising:

inputting an inhibitory circuit to an excitatory circuit, which is to be activated by a first trigger that is a stimulus or a task for a living body, by applying a second trigger which is lower in intensity than the first trigger in advance of the first trigger, wherein an action of the inhibitory circuit on the excitatory circuit is evaluated on the basis of attenuation caused by the input of the inhibitory circuit in brain activity induced by activation of the excitatory circuit, (Clause 14) A method for evaluating a drug to be used for a disease related to an inhibitory circuit, the method comprising:

inputting an inhibitory circuit to an excitatory circuit, which is to be activated by a first trigger that is a stimulus or a task for a living body to which the drug has been administered, by applying a second trigger which is lower in intensity than the first trigger in advance of the first trigger; and inputting an inhibitory circuit to an excitatory circuit, which is to be activated by a first trigger that is a stimulus or a task for a living body to which the drug has not been administered, by applying a second trigger which is lower in intensity than the first trigger in advance of the first trigger, wherein the drug is evaluated on the basis of attenuation caused by the input of the inhibitory circuit in brain activity induced by the activation of the excitatory circuit in the living body to which the drug has been administered and the living body to which the drug has not been administered.

(Clause 15) A screening method for a drug to be used for a disease related to an inhibitory circuit, the method comprising:

inputting an inhibitory circuit to an excitatory circuit, which is to be activated by a first trigger that is a stimulus or a task for a living body to which the drug has been administered, by applying a second trigger which is lower in intensity than the first trigger in advance of the first trigger; and inputting an inhibitory circuit to an excitatory circuit, which is to be activated by a trigger that is a stimulus or a task for a living body to which the drug has not been administered, by applying a second trigger which is lower in intensity than the first trigger in advance of the first trigger, wherein the drug which enhances or reduces an action of the inhibitory circuit is screened on the basis of attenuation caused by the input of the inhibitory circuit in brain activity induced by the activation of the excitatory circuit in the living body to which the drug has been administered and the living body to which the drug has not been administered.

(Clause 16) A detection system for an inhibitory circuit, comprising:

a detection device that detects electrical activity based on brain activity; and a device capable of applying, to a living body, a first trigger that is a stimulus or a task for the living body, and capable of applying a second trigger in advance of the first trigger, the second trigger being lower in intensity than the first trigger, wherein attenuation of brain activity caused by application of the second trigger is detected by acquiring first brain activity information on brain activity induced by the application of the first trigger, and second brain activity information on brain activity induced by the application of the first trigger accompanied by the second trigger.

(Clause 17) A detection system for an inhibitory circuit of a brain, the method comprising:

a detection device that detects electrical activity based on brain activity;

a device capable of applying, to a living body, a first trigger that is a stimulus or a task for the living body, and capable of applying a second trigger in advance of the first trigger, the second trigger being lower in intensity than the first trigger, wherein attenuation of brain activity caused by application of the second trigger is detected by acquiring first brain activity information on brain activity induced by the application of the first trigger, and second brain activity information on brain activity induced by the application of the first trigger accompanied by the second trigger.

(Clause 18) The system according to (Clause 17), wherein the excitatory circuit is a response circuit for a change in the trigger.

(Clause 19) The system according to (Clause 17) or (Clause 18), wherein the excitatory circuit is a response circuit related to one or two or more selected from. the group consisting of a sense of touch, a sense of temperature, a sense of pain and deep sensibility, which are somatic sensations, a sense of vision, a sense of hearing, a sense of taste, and a sense of smell.

(Clause 20) The system according to any one of (Clause 17) to (Clause 19), wherein the excitatory circuit is a response circuit related to a sense of hearing.

(Clause 21) The system according to any one of (Clause 17) to (Clause 20), wherein the excitatory circuit is a response circuit for a sound pressure change.

(Clause 22) The system according to any one of (Clause 17) to (Clause 21), wherein the inhibitory circuit is one or both of a GABA-A mediating inhibitory circuit arid a GABA-B mediating inhibitory circuit.

(Clause 23) The system according to any one of (Clause 17) (Clause 22), wherein the input of the inhibitory circuit is implemented in a range of 10 ms or more and 800 ms or less in advance of the supply of the trigger.

(Clause 24) The system according to any one of (Clause 17) to (Clause 23), wherein the input of the inhibitory circuit is implemented in any one or both of a range of 10 ms or more and 30 ms or less and a range of 500 ms or more and 700 ms or less in advance of the application of the trigger.

(Clause 25) The system according to any one of (Clause 17) to (Clause 24), wherein the action of the inhibitory circuit is evaluated on the basis of the first brain activity information and the second brain activity information.

(Clause 26) The system according to any one of (Clause 17) to (Clause 5 wherein the brain activity is detected by electrical activity based on brain activity.

(Clause 27) The system according to any one of (Clause 17) to (Clause 26), wherein the brain activity is detected by using an electroencephalogram or a magnetoencephalogram.

(Clause 28) A method for actuating a detection system for an inhibitory circuit of a brain, the method comprising:

the trigger output device outputting a first trigger that is a stimulus or a task and outputs a second trigger in advance of the first trigger; and the brain activity detection device acquiring second brain activity information on brain activity induced by the application of the first trigger which is accompanied by the application of the second trigger, and detects attenuation of brain activity caused by the application of the second trigger.

(Clause 29) The method according to (Clause 28), comprising:

the trigger output device outputting the first trigger; and the brain activity detection device acquiring first brain activity rmation on brain activity induced by the application of the first trigger.

(Clause 30) A method for examining a disease related to an inhibitory circuit, the method comprising:

inputting an inhibitory circuit to an excitatory circuit, which is to be activated by a first trigger that is a stimulus or a task for a living body, by applying a second trigger which is lower in intensity than the first trigger in advance of the first trigger, wherein an action of the inhibitory circuit on the excitatory circuit is evaluated on the basis of attenuation caused by the input. of the inhibitory circuit in brain activity induced by the activation of the excitatory circuit.

(Clause 31) A method for evaluating a drug to be used for a disease:related to an inhibitory circuit, the method comprising:

inputting an inhibitory circuit to an excitatory circuit, which is to be activated by a first trigger that is a stimulus or a task for a living body to which the drug has been administered, by applying a second trigger which is lower in intensity than the first trigger in advance of the first trigger; and the system inputting an inhibitory circuit to an excitatory circuit, which is to be activated by a first trigger that is a stimulus or a task for a living body to which the drug has not been administered, by applying a second trigger which is lower in intensity than the first trigger in advance of the first trigger, wherein the drug is evaluated on the basis of attenuation caused by the input of the inhibitory circuit in brain activity induced by the activation of the excitatory circuit in the living body to which the drug has been administered and the living body to which the drug has not been administered.

(Clause 32) A screening method for a drug to be used for a disease related to an irrinibitory circuit, the method comprising:

inputting an inhibitory circuit to an excitatory circuit, which is to be activated by a first trigger that is a stimulus or a task for a living body to which the drug has been administered, by applying a second trigger which is lower in intensity than the first trigger in advance of the first trigger; and inputting an inhibitory circuit to an excitatory circuit, which is to be activated by a trigger that is a stimulus or a task for a living body to which the drug has not been administered, by applying a second trigger which is lower in intensity than the first trigger in advance of the first trigger, wherein the drug which enhances or reduces an action of the inhibitory circuit is screened on the basis of attenuation caused by the input of the inhibitory circuit in brain activity induced by the activation of the excitatory circuit in the living body to which the drug has been administered and the living body to which the drug has not been administered.

Embodiments

Hereinafter, specific examples embodying the present disclosure will be described, but the following specific examples are for illustrating the present disclosure and are not intended to be limiting.

First Embodiment

In the present embodiment, an action of inhibitory circuits of 13 humans was evaluated using an excitatory circuit for a change response to a sound pressure change in an auditory system. As for the change response, when a sudden slight increase in sound pressure (10 dB) is generated in a background sound in which a short click sound (70 dB) of 1 ms is continuously generated at a frequency of 100 Hz, the human brain reacts thereto with very high sensitivity and a remarkable brain response is triggered.

In the present embodiment, an evaluation syste was constructed in the following manner for evaluating the inhibitory circuit.

The evaluation system included a stimulus output unit and a brain activity measurement unit. As shown in FIG. 1A, the stimulus output unit was configured capable of outputting stimuli in the following three modes: a test stimulus pattern in which a click sound (1 ms) with increased sound pressure (10 dB) was generated with respect to the above-described background sound (70 dB) at the time of 400 ms from the start of the background sound (upper part of FIG. 1A), a preceding stimulus pattern in which only click sounds (1 ms) with a sound pressure increased twice by 5 dB were generated with respect to the background sound after predetermined times (30 ms and 60 ms preceding a sound pressure increase of 10 dB) (lower part of FIG. 1A), and a pattern (test+preceding stimulus) in which the aforementioned patterns were combined (middle part of FIG. 1A).

Full-head measurement with the cerebral magnetic field measurement unit was performed using a magnetoencephalograph (306 channel magnetoencephalograph (Vector View, Neuromag, Helsinki, Finland)).

Three kinds of stimuli, namely, the test stimulus, the preceding stimulus, and the test+preceding stimulus were sequentially applied to the subject at regular intervals from the stimulus output irnit through an insert earphone from the start of the test, and brain activity induced by the activation of the excitatory circuit at this time was measured as a cerebral magnetic field. As shown in FIG. 1A, the test stimulus was presented at 400 ms and the preceding stimulus (two click tones of 1 ms) was presented 30 ms and 60 ms in advance of the start of the test stimulus. A predetermined number of trials could be designated in the cerebral magnetic field measurement unit, addition was performed automatically, and an attenuation rate (inhibition rate) was obtained from the amplitude of the addition waveform. The results are shown in FIG. 18 (n=13, right hemisphere).

Figure 1B:
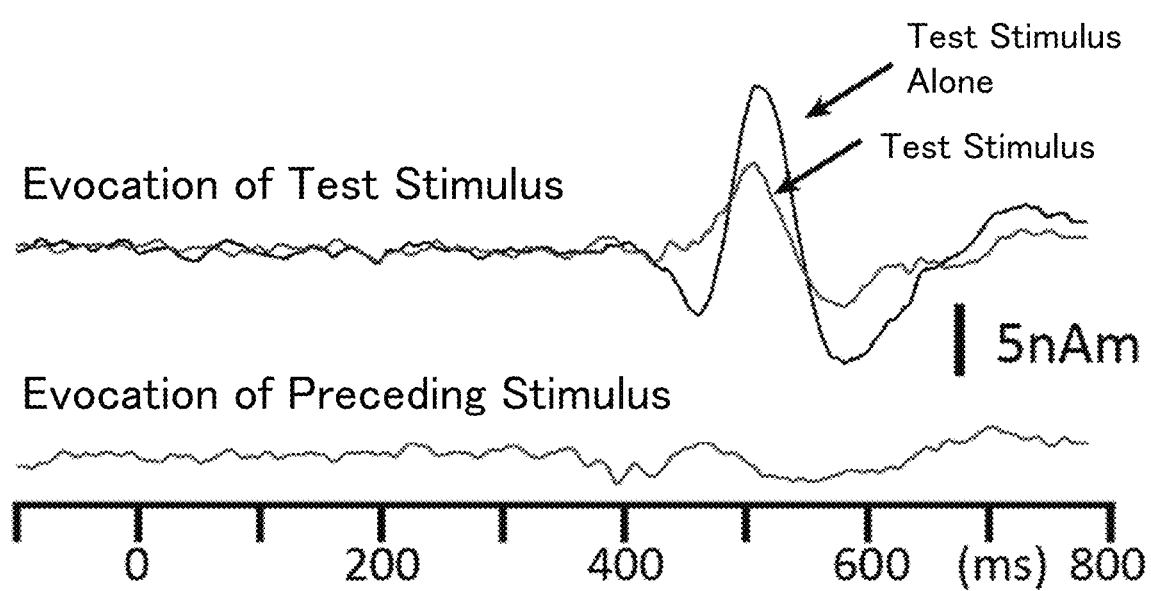
FIG. 1B is a diagram showing an addition brain activity obtained as an evaluation result of the inhibitory circuit in the first embodiment.

As shown in the upper part of FIG. 1B, the brain activity amplitude of the test+preceding stimulus was attenuated more than the amplitude of the test stimulus. As shown in the lower part of FIG. 1B, an activity waveform of only the preceding stimulus was itself a weak one triggering only a slight brain response.

As described above, it was found from the amplitude of the brain activity waveform of the test+preceding stimulus that brain activity was attenuated by the preceding stimulus. That is, it was found that brain activity induced by the test stimulus (the first trigger) was attenuated by the application of the preceding stimulus (the second trigger). The inventors of the present invention confirmed that in the abovementioned test system, this attenuation is active inhibition by the inhibitory circuit and is not caused by the excitatory circuit itself or the like. That is, by applying the preceding stimulus in various patterns (number of times, timing), it is confirmed that evocation and inhibition of response proceed by different routes.

Second Embodiment

Figure 2:
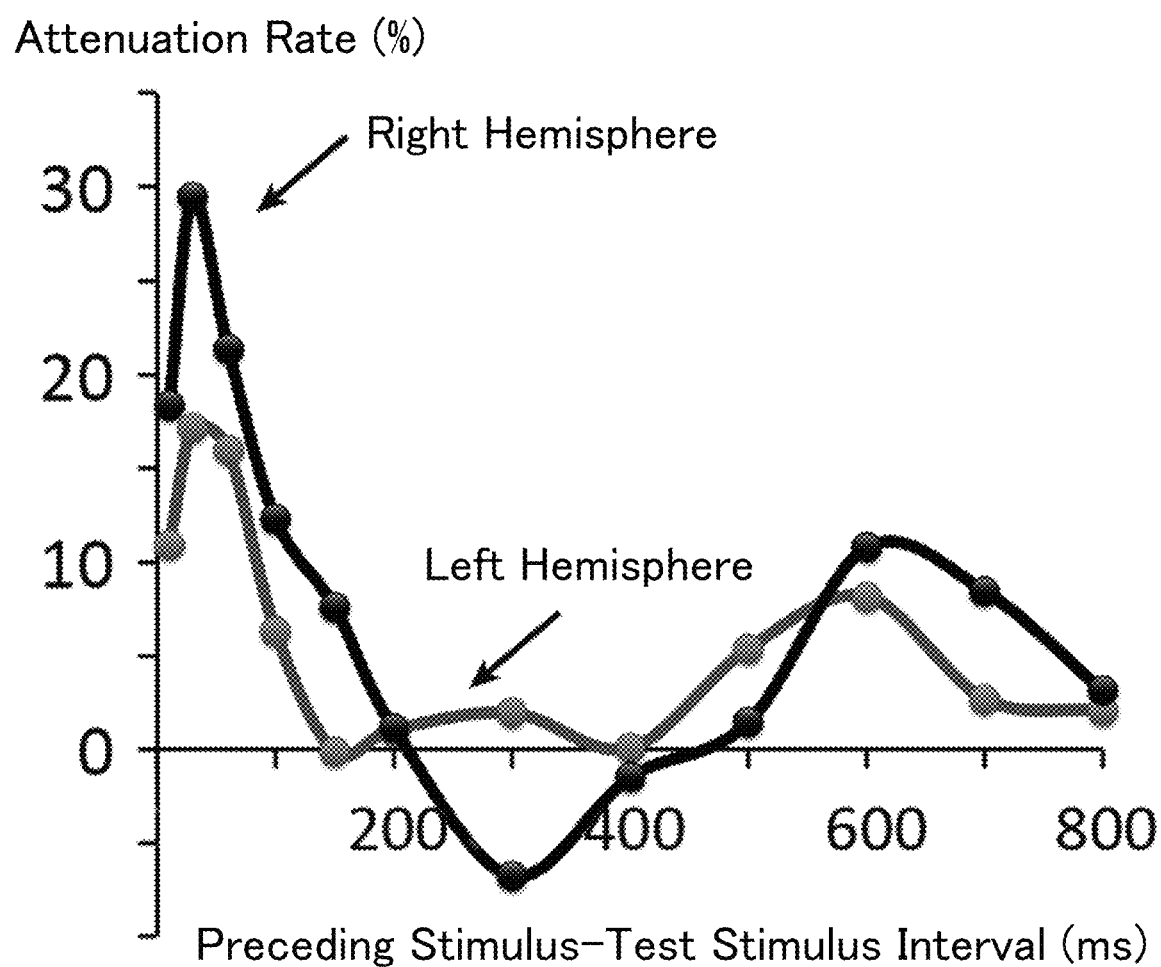
FIG. 2 is a diagram showing an attenuation rate obtained as a result of applying a preceding stimulus from 10 ms to 800 ms in advance of a test stimulus.
Figure 3:
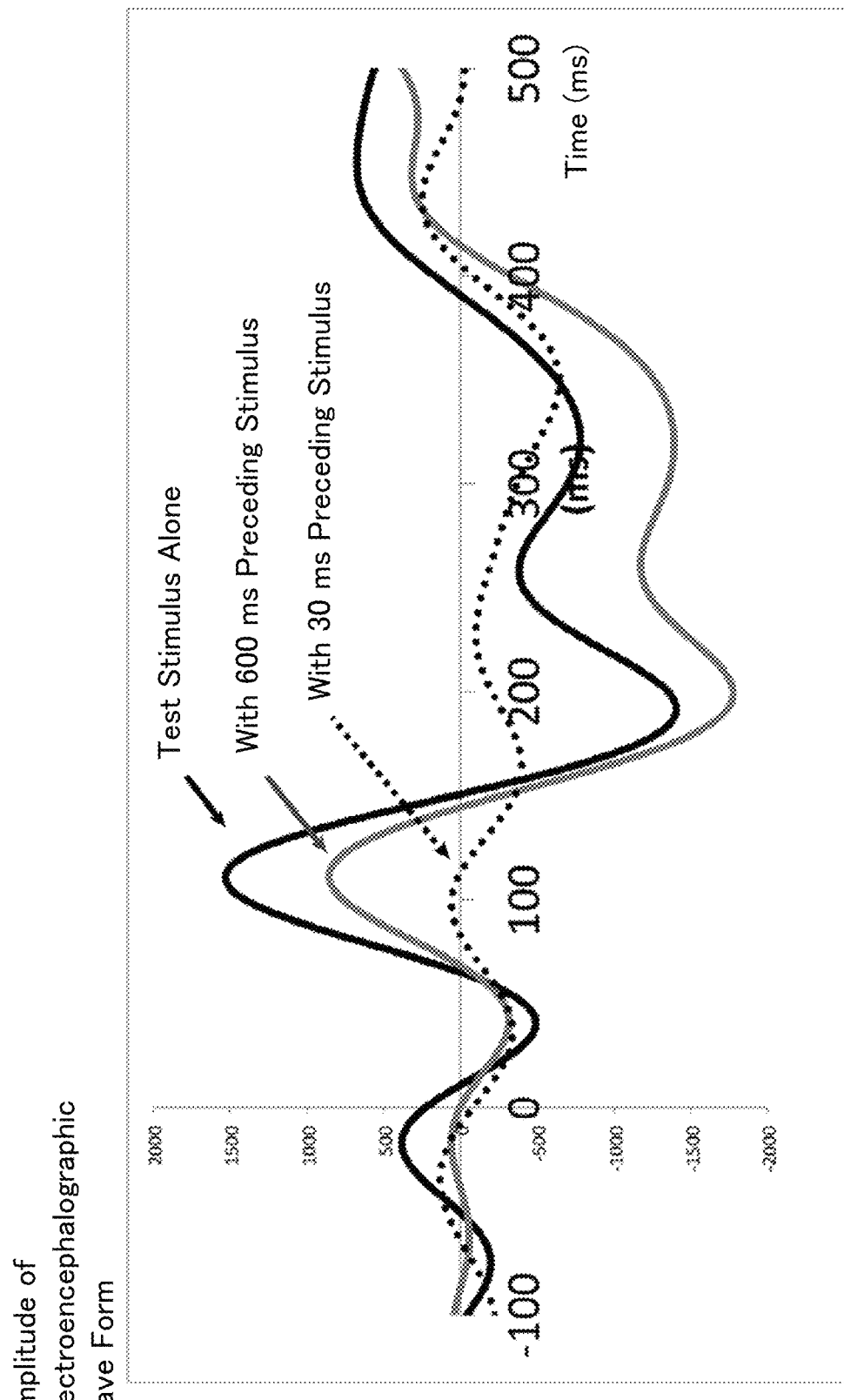
FIG. 3 is a diagram showing an electroencephalographic waveform when a preceding stimulus is applied 30 ms and 600 ms in advance of the test stimulus, and relative values recorded by an electroencephalograph are plotted against the ordinate.

In the present mbodiment, the brain magnetic field was measured and the attenuation rate was obtained from the amplitude of the waveform by applying a test stimulus by using the same background sound as in the first embodiment to the same test population group as in the first embodiment and also applying click sounds (1 ms) increased by 5 dB at appropriate intervals in a range from 10 ms to 800 ms in advance of the application of the test stimulus. The results are shown in FIG. 2. Also, FIG. 3 shows the electroencephalographic waveform derived when 30-ms and 600-ms preceding stimuli and a test stimulus were applied to one subject to be tested and the electroencephalographic waveform derived when only the test stimulus was applied to the same subject. The electroencephalographic measurement was performed using a normal evoked electroencephalograph (Neuropack, Nihon Kohden), and the electroencephalographic electrodes were attached to predetermined parts (in a ease of the sense of hearing, the best inducement conceivable from the results of the cerebral magnetic field measurement was Fz—bilateral Mastoid).

As shown in FIG. 2, the action of the inhibitory circuit was clearly bimodal. The peak of an early inhibition was around 30 ms to 60 ms, a late inhibition was around 600 ms, and the maximum attenuation rate was 17% in a left hemisphere and 30% in a right hemisphere, and 8% in the left hemisphere and 11% in the right hemisphere, respectively. In the late inhibition, the threshold was high and a significant inhibition was only at 600 ms. The early inhibition and the late inhibition were thought to be due to different mechanisms.

Further, it was found that these two inhibitions can be clearly observed from the electroencephalographic waveform, as shown in FIG. 3.

Furthermore, in the present embodiment, a more detailed study was performed by applying a 5 dB enlarged click sound (1 ms) at an appropriate interval in a range of 10 ms to 70 ins in advance of the test stimulus with respect to an early component. The results are shown in FIG. 4.

Figure 4:
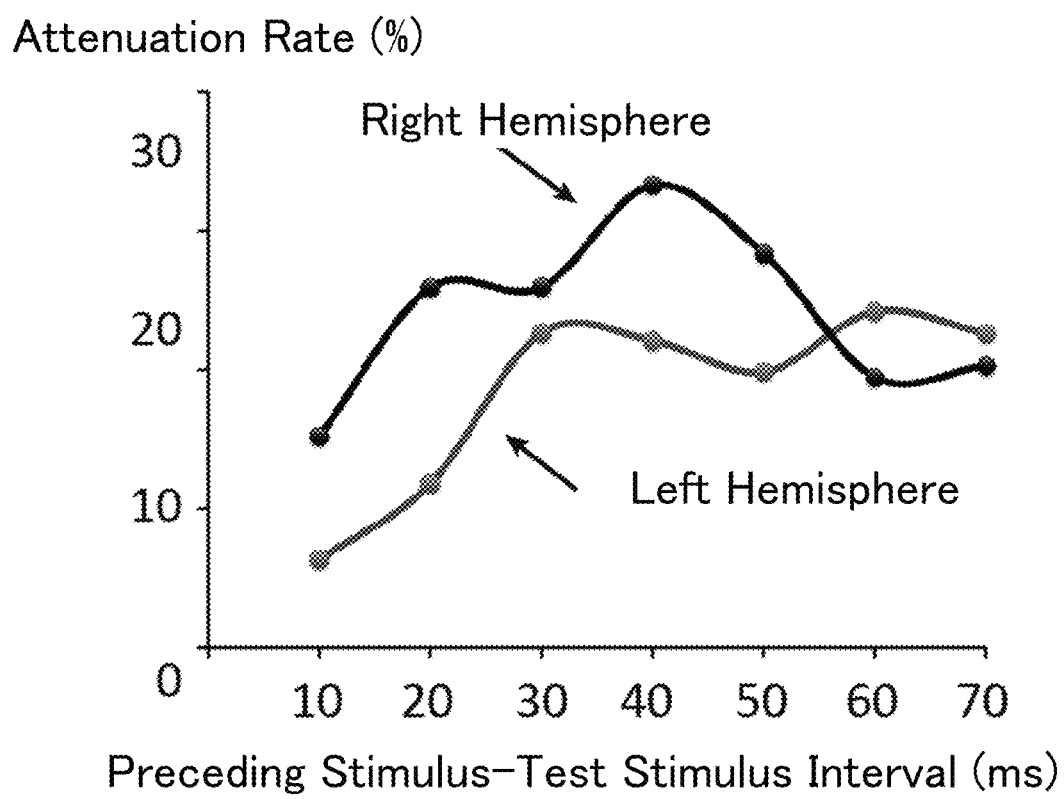
FIG. 4 is a diagram showing an attenuation rate obtained as a result of applying a preceding stimulus from 10 ms to 70 ms in advance of the test stimulus.

As shown in FIG. 4, it was found that two types of inhibition mechanisms were further included in each of the early components. Each of these early components was thought to be classifiable into two types: 20 ms to 30 ms inhibition and 40 ms to 60 ms inhibition. These were thought to be due to different inhibition mechanisms. in FIG. 4, even when the preceding stimulus—test stimulus interval is 5 ms, the attenuation rate is about 5% to 10%, which indicates that sufficient detection is possible.

Third Embodiment

Figure 5:
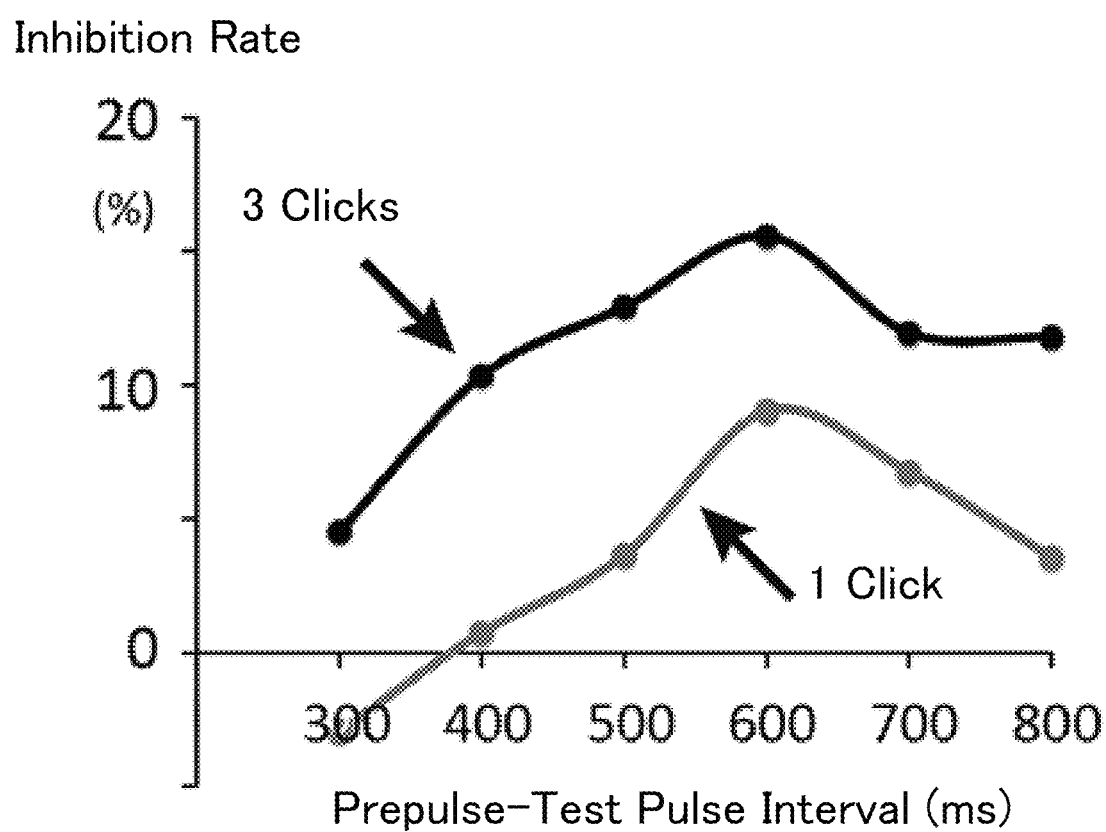
FIG. 5 is a diagram showing an inhibition rate obtained by changing the intensity of a preceding stimulus in a case where the preceding stimulus is applied from 300 ms to 800 ms in advance of a test stimulus.
Figure 6:
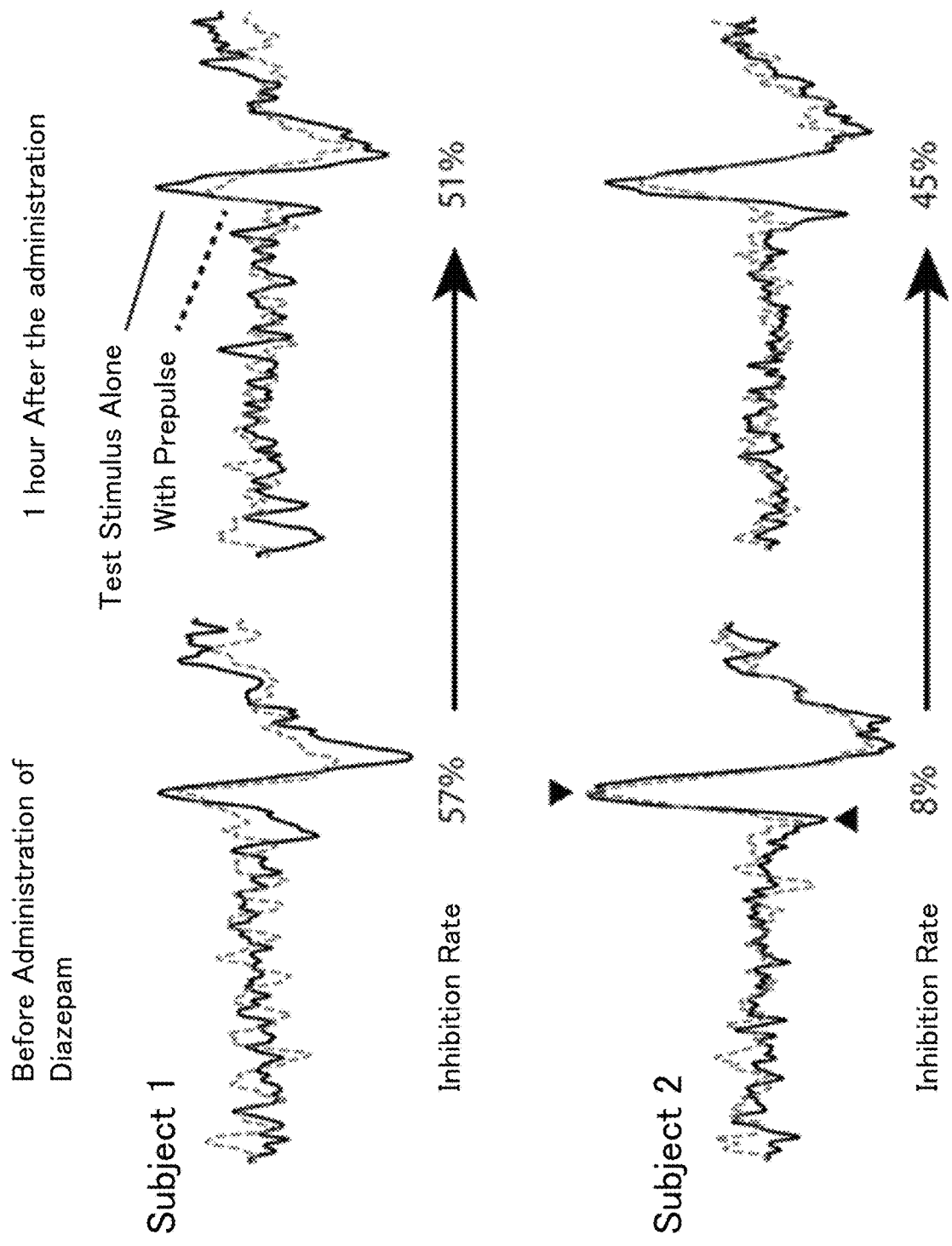
FIG. 6 is a diagram showing addition brain activity and inhibition rate obtained as results of evaluating an inhibitory circuit in advance of administration of diazepam to Subject 1 and Subject 2, and 1 hour after the administration.

In the present embodiment, an influence of the stimulus intensity (prepulse intensity) of the preceding stimulus was observed (N=9). Changes in an inhibition rate over an elapsed time in a case where a prepulse (increase of 5 dB from the baseline) was inserted 300 ms to 800 ms in advance of the test stimulus into the background sound similar to that in the first embodiment in the same recording procedure as in the first embodiment was compared for a case of a weak prepulse in the form of one-shot click sound and a case of a strong prepulse in the form of three clicks. As shown in FIG. 5, although the inhibition rate is stronger in the case of the prepulse in the form of three clicks, it can be seen that the change in inhibition over time is not different between the two cases. When the prepulse intensity is increased, the attenuation is caused by the mechanism only in the excitatory circuit, such as a refractory period and synaptic fatigue, and a weak test stimulus is sometimes observed without the intervention of the inhibitory circuit, but with respect to the inhibition in the present embodiment, it is clear that the influence of the refractory period, synaptic fatigue and the like on the inhibition is small even though the preceding stimulus is not weak. By such verification, it is possible to set a test system in which a response attenuation factor other than inhibitory mediating cells can be observed when a strong prepulse is used, it is possible to verify whether the inhibition reflects the function of inhibitory mediating cells, and the inhibitory circuit is evaluated without necessarily using a weak preceding stimulus. Further, in the present embodiment, it is clear that the measurement result of 300 ms for one click is enhanced by preceding stimulus. Since a brain activity which is thus caused by the preceding stimulus can be observed not only as attenuation but also as enhancement, it is important to observe how the brain activity is changed by the input of the inhibitory circuit. Further, in the present embodiment, the prepulse intensity is changed by a number of repeated clicks, but it may be also changed by an increase amount from the base line.

By using the same method as in the present embodiment, it is possible to set the stimulus conditions for the preceding stimulus and test stimulus under which the test stimulus is attenuated by the mechanism only in the excitatory circuit such as a refractory period and synaptic fatigue without the participation of the inhibitory circuit. Also when such a stimulus is used, the stimulus setting is the result of evaluating the inhibitory circuit and is included in the present invention.

Fourth Embodiment

The present embodiment relates to an evaluation method and a screening method for a drug to be used for a disease relating to an inhibitory circuit. Effect of diazepam (5 mg single oral administration) on inhibition was examined by comparing the inhibition rates before and after the administration of the drug to two subjects of different types by the same recording procedure as in first embodiment. The amplitude of the response was taken between vertices of a component of 50 ms and a component of 100 ms (black triangles). The results are shown in FIG,. 6. Comparing the inhibition rates before the diazepam administration (left side in the figure) and after the administration (right side in the figure), in Subject 1, the inhibition was strong before the administration of diazepam and there was little change after the administration. Subject 2 represents an example with a weak early inhibition, which is significantly lower than and the average value (about 30%), but the inhibition rate after the administration was 45%, which is the same level as in Subject 1. That is, it can be determined that diazepam has a strong effect on Subject 2 and a small effect on Subject 1. By such a method, it is possible to determine whether or not the drug selected for each subject is appropriate, and to grasp follow-up of the treatment. Further, although studies using slice specimens indicate that diazepam enhances GABA-A early inhibition due to basket cells, the method for the present embodiment can reliably confirm that this inhibition is via GABA-A receptors. Thus, the present method can be used for evaluating and developing drugs.

Fifth Embodiment

Figure 7:
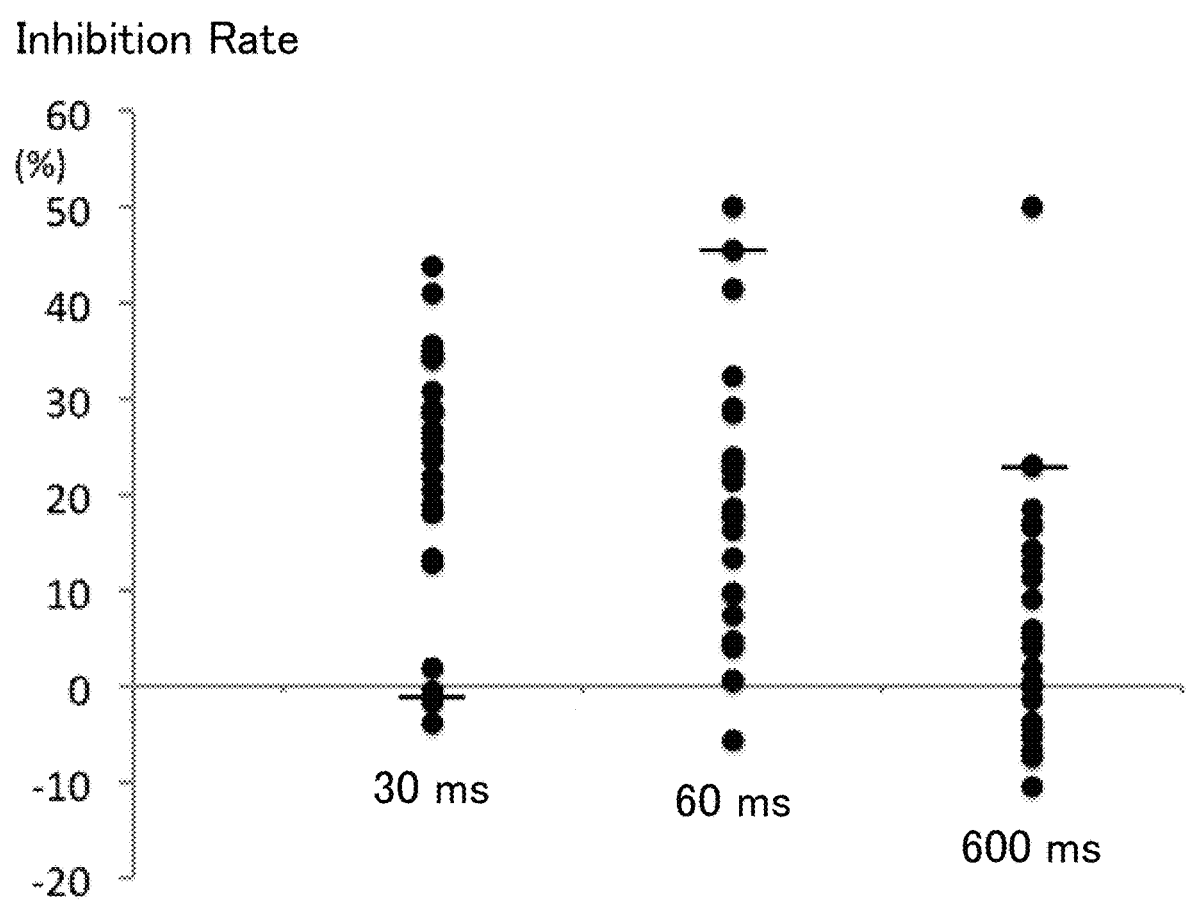
FIG. 7 is a diagram in which distribution of inhibition rates is plotted against 30-ms, 60-ms, and 600-ms preceding stimulus performed for 25 subjects.

The present embodiment is a method for selecting a drug to be used for a disease related to an inhibitory circuit. Fourth embodiment related to a method for evaluating the effect after drug administration for each individual, whereas in fifth embodiment, a drug suitable for each individual is selected in advance of drug administration. FIG. 7 is a graph showing inhibition rate distributions for 30 ms, 60 ms, and 600 ms acquired by the methods described in first and second embodiments (N=26 hemispheres). In FIG. 7, black circles (●) indicate data of individuals. Each inhibition rate is widely distributed from negative values to about 50%, reflecting individual differences. It is shown that individual characteristics can be evaluated at a certain level with respect to the functions of the inhibitory system. Here, a horizontal bar is added to the result for a certain subject. In this subject, there is no early inhibition at 30 ms, whereas both late inhibition at 60 ms and late inhibition at 600 ms are high. erefore, it can be determined that the function of basket cells via the GABA-A receptors is weak, so that a drug acting on the GABA-A receptors, such as diazepam, can be selected as a suitable drug. Meanwhile, a drug to be used for a disease related to an inhibitory circuit, this drug being tailored to the individual, can be selected in advance of drug administration by measuring the individual characteristics of inhibitory circuits. For example, when the inhibition rate at 30 ms and 600 ms is low although sufficient inhibition is realized at 60 ms, a drug targeting the GABA-A receptors can be selected; when the inhibition rate is poor at all of 30 ms, 60 ms and 600 ms, it is determined that GABA or GABA receptors are not functioning, so a drug targeting GABA or GABA receptors can be selected; and when the inhibition rate at 30 ms and 60 ms is high and the inhibition rate is low at 600 ms only, it can be determined that Martinotti cells are not functioning, so a drug targeting Martinotti cells can be selected.

Sixth Embodiment

Figure 8:
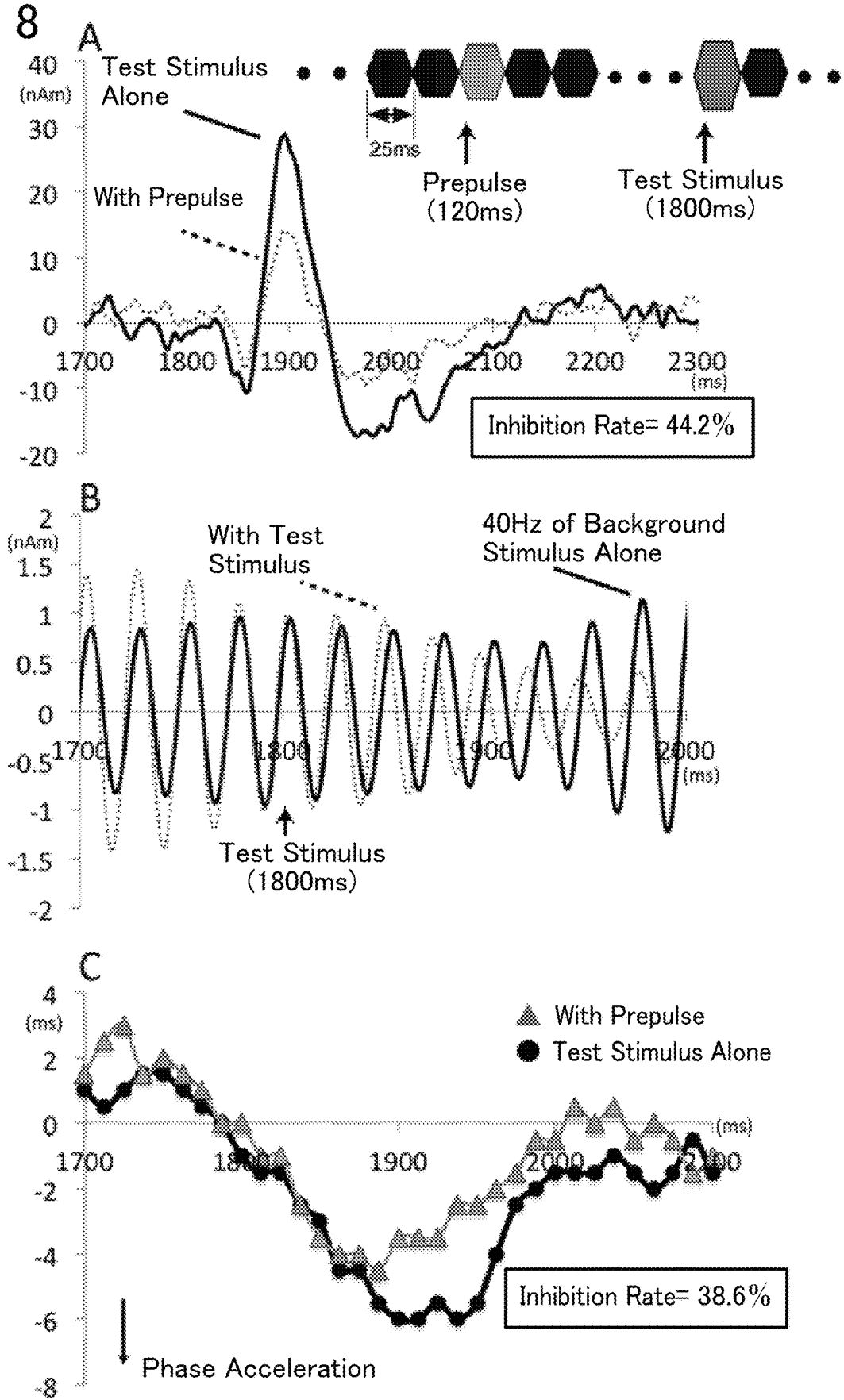
FIG. 8A is a diagram showing a sound stimulus pattern (upper right) in sixth embodiment and addition waveforms of the brain activity at the time of presentation of the ound stimulus pattern and inhibition by prepulse.
FIG. 8B is a diagram showing a steady-state brain activity when only a background stimulus is used and how a phase of brain activity is accelerated by presentation of the test stimulus.
FIG. 8C is a diagram obtained by calculating an inhibition rate from a change in phase in a case where only a test stimulus is applied with respect to the background stimulus and a case where a prepulse is present.

In the present embodiment, the results obtained by comparing the input of the inhibitory circuit for changes in the cerebral evoked response amplitude (magnitude of brain activity) and that for changes in latency of the steady-state auditory evoked reaction (time in which brain activity occurs) are shown as an example of detecting the input of the inhibitory circuit by the change in time (latency) in which brain activity occurs. As shown in the upper right portion of FIG. 8A, pure tones (1000 Hz) as stimulus sound of 65 dB and 25 ms were connected, without gaps, as a background brain activity and a steady-state auditory evoked reaction of 40 Hz was evoked. At a point of 1800 ms from the beginning of this sequence of sound pulses, one pure tone of 25 ms was made 15 dB stronger than the background and this was taken as a test stimulus (corresponding to the first trigger). Brain activity caused by this test stimulus is brain activity caused by the first trigger. A pulse in which one pure tone of 80 dB was inserted 600 ms iia advance of the test stimulus was set as a prepulse (corresponding to the second trigger) to evaluate the inhibitory circuit. For brain activity, addition waveforms were recorded with the same magnetoencephalograph as in the first embodiment with respect to four kinds of simulation: background stimulus only, background stimulus test stimulus, background stimulus+prepulse, and background stimulus+prepulse+test stimulus. FIG. 8 shows measurement results for a certain subject. FIG. 8A shows a comparison of changes in brain activity in the case of a test stimulus alone and the case of a test stimulus+prepulse simulation (with a prepulse), that is, a comparison between first brain activity information and second brain activity information. The magnitude (amplitude) of brain activity was clearly attenuated in the case of prepulse (dotted line) as compared with the ease of the test stimulus alone (black line), and the inhibition rate calculated at their apex amplitudes was 44.2%.

Next, FIG. 8B shows a 40 Hz steady-state brain reaction obtained by applying a bandpass filter of 40 Hz⊥10 Hz with respect to background stimulus alone and background stimulus+test stimulus. In a case of only background stimulus, since the sound. stimulus used is repetition of pure tones of 25 ms, a response activity of 40 Hz is triggered in the brain (solid line in FIG. 8B). Thus, in a case of only background stimulus, a sinusoidal curve of 40 Hz with a regular rhythm is obtained. Meanwhile, where a test stimulus (corresponding to the first trigger) is applied at 1800 ms, the waveform changes as shown by the dotted line in FIG. 8B, and from about 1850 ms to 2000 ms, the peak of the sinusoidal curve is shifted to earlier timing. This is the "phase acceleration" by the test stimulus (change-related brain activity). This phase acceleration is the first brain activity information on brain activity caused by the change in the first trigger. FIG. 8C shows how the phase accelerates for the test stimulus alone and for the test stimulus+prepulse (corresponding to the second trigger). A negative value on the ordinate indicates that the phase speeded up with respect to the reference brain activity (only the background stimulus), that is, the phase was accelerated. Triangles show the change in phase when the prepulse is present, and it is clear that the degree of change decreases as compared with the case of the test stimulus alone (black circles). That is, it is clear that the inhibitory circuit has been input by the application of the second trigger. When comparing the phase change amounts by the integral values in the section from 1850 ms to 2050 ms, the calculated inhibition rate is 38.6%. Thus, even by using the change in the interval of time (the change in rhythm) during Which brain activity occurs, it is possible to calculate the inhibition rate of the same degree as the inhibition rate obtained from the change in the magnitude of the brain activity, and the inhibitory circuit can be evaluated also by the change in the interval of time during which brain activity occurs.

Seventh Embodiment

The present embodiment relates to a method for measuring and analyzing the inhibitory circuit characteristics of a prospective spectacle lens purchaser. The inhibitory circuit characteristics were evaluated in the following manner. Thus, the evaluation was performed in accordance with a visual acuity test of the user performed at a spectacle shop, by an ophthalmologist and the like with respect to a spectacle lens purchaser. A figure constituted by line segments was presented to a certain spectacle lens purchaser 1 on a display at a stimulus interval (15 Hz) of 66.67 ms, and a steady-state visual evoked reaction was evoked as a background brain wave. Then, the test stimulus (corresponding to the first trigger) was obtained by changing a luminance of the figure. Brain activity caused by this test stimulus is brain activity caused by the change in the first trigger. In the present embodiment, the luminance of the figure is increased by a factor of 1.5, but it is not particularly limited thereto, and similar brain activity (change-related brain activity) can also be measured when, for example, the luminance is decreased by half For example, the luminance may be changed by 10% to 20%.

Figure 9A:
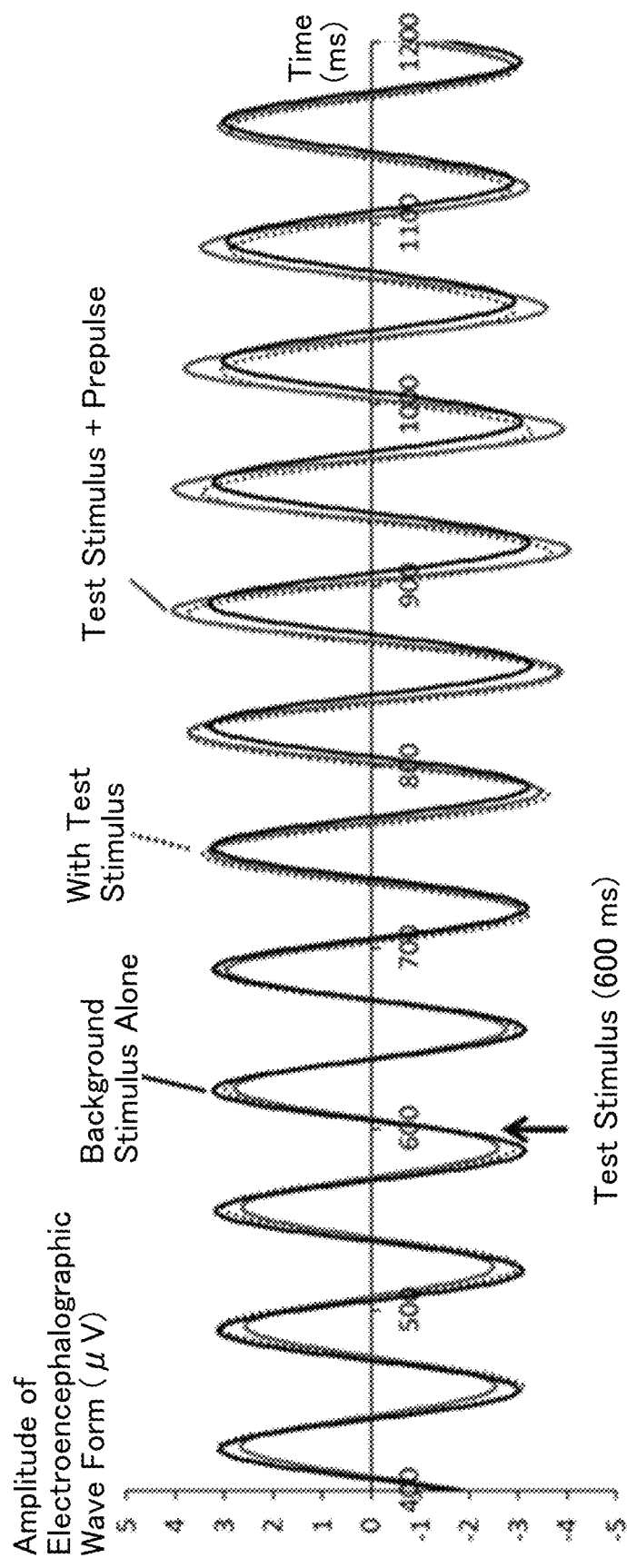
FIG. 9A is a diagram showing brain activity in a case of using a visual stimulus, a phase acceleration caused by addition of a test stimulus to the background stimulus, and inhibition caused by a prepulse in seventh embodiment.
Figure 9B:
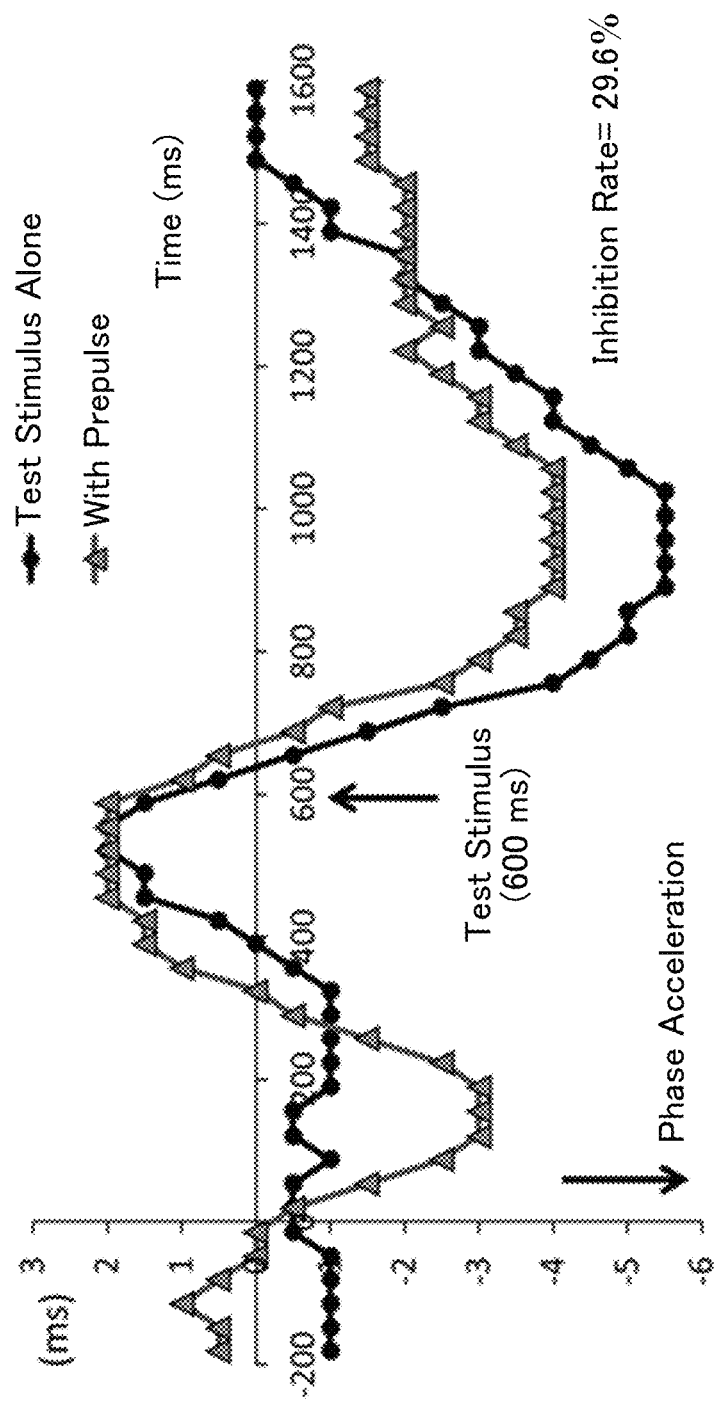
FIG. 9B is a diagram obtained by calculating an inhibition rate from a change in phase in a case where only a test stimulus is applied with respect to the background stimulus and in a case where a prepulse is present, by using a visual stimulus.

An electroencephalograph was used for brain activity recording, electrodes were attached to Oz-Fz in the International 10-20 electrode method, and the differential potential between Oz and Fz was recorded. FIG. 9A shows results obtained by applying a 13-17 Hz band pass filter to a measured addition waveform with respect to Subject 1. The test stimulus, which was the first trigger, was confirmed to accelerate a phase over about 50 ms to 600 ms after the stimulus. It was found from FIGS. 9A and 9B that this phase acceleration was inhibited by a prepulse stimulus (corresponding to the second trigger) presented 600 ms in advance of the test stimulus. The inhibitory circuit could thus be evaluated even by using the visual stimulus. Here, the inhibition rate was found to be 29.6% from FIG. 9B. Further, similarly to sixth embodiment, it was also possible to evaluate the inhibitory circuit by the change in the amplitude of brain activity by measuring the change-related potential with respect to the test stimulus without applying the band pass filter. In the present measurement result, the inhibition rate was 28%. It is clear that even in a case of visual stimulus, similarly to sixth embodiment, by using the change in the interval of time (change in rhythm) during which brain activity occurs, it is possible to calculate the inhibition rate of the same degree as the inhibition rate obtained from the change in the magnitude of brain activity.

In the present embodiment, the follow arrangement is also unrestricted. For example, in the diagram showing the phase change in FIG. 9B, change-related brain activity (phase acceleration) caused by the prepulse is observed over 200 ms from the presentation of the prepulse (presented at 0 ms). In order to evaluate the characteristics of the inhibitory circuit, continuous background stimulus (for example, steady-state brain activity) can be taken as the first brain activity information, and the characteristics of the inhibitory circuit can be evaluated by analyzing the change in the first brain activity information caused by the prepulse. Further, for example, the inhibitory circuit may be evaluated by change in the phase when the intensity of the prepulse is changed variously, Such arrangements are unrestricted and are included in the disclosure of the present description.

CITATION LIST

Non Patent Literature 1: Kujirai T et al. Corticocortical inhibition in human motor cortex. Journal of Physiology (London) 471: 501-519, 1993.

The invention claimed is:

1. A system, the system comprising:
    a detection device that detects a brain activity by way of detecting electrical activity of the brain or by way of detecting a change in cerebral blood flow;
    a trigger output device that outputs a first trigger that is a stimulus or a task for a living body, and a second trigger that can change a first brain activity induced by an output of the first trigger,
        wherein, for the first trigger, the stimulus is selected from the group consisting of a visual stimulus and a sound;
    means for acquiring first brain activity information on the first brain activity;
    means for acquiring second brain activity information on a second brain activity induced by the output of the first trigger which is accompanied by the output of the second trigger;
    means for detecting a change in the first brain activity induced by the output of the second trigger based on the first brain activity information and the second brain activity information; and
    means for selecting a type of inhibitory circuit to be inputted to an excitatory circuit which is to be activated by the first trigger, wherein the inhibitory circuit is selected according to a timing of the output of the second trigger in advance of the output of the first trigger.

2. The system according to claim 1, wherein the inhibitory circuit is one or both of a GABA-A mediating inhibitory circuit and a GABA-B mediating inhibitory circuit.

3. The method according to claim 1, wherein the inhibitory circuit is one or both of a GABA-A-ergic inhibitory interneuron and a GABA-B-ergic inhibitory interneuron.

4. The system according to claim 3, wherein the GABA-A-ergic inhibitory interneuron is one or both of an inhibitory circuit formed by a basket cell and an inhibitory circuit formed by a Martinotti cell.

5. The system according to claim 1, wherein the first brain activity information is information on a response circuit for a change in the first trigger.

6. The system according to claim 1, wherein the first brain activity information is information on a response circuit related to one, or both, of a sense of vision and a sense of hearing.

7. The system according to claim 1, wherein the first brain activity information is information on a response circuit related to a sense of hearing and is information on a response circuit for a sound pressure change.

8. The system according to claim 1, wherein the output of the second trigger is implemented in any one or both of a range of 20 ms or more and 30 ms or less and a range of 40 ms or more and 60 ms or less in advance of the output of the first trigger.

9. The system according to claim 1, wherein the output of the second trigger is implemented in a range of 500 ms or more and 700 ms or less in advance of the output of the first trigger.

10. The system according to claim 1, wherein the change in the first brain activity is [a change of the first brain activity] induced by the input of the inhibitory circuit, and one or two selected from the group consisting of a change of a time (latency) in which the first brain activity occurs and a change of a location (movement) where the first brain activity occurs.

11. The system according to claim 1, wherein the change in the first brain activity is [a change of the first brain activity] induced by the input of the inhibitory circuit, and a change of a rhythm of the first brain activity.

12. The system according to claim 1, further comprising means for executing output processing of information on the inhibitory circuit.

13. The system according to claim 1, wherein the system detects a type of an inhibitory interneuron and/or receptor related to the inhibitory circuit.

14. The system according to claim 1, wherein the detection device detects electrical brain activity as the brain activity.

15. The system according to claim 1, wherein the system produces an inhibitory circuit characteristic output capable of being used to produce a product.

16. The system according to claim 1, wherein the detection device is selected from the group consisting of a device that performs electroencephalography, a device that performs magnetoencephalography, a functional magnetic resonance imager (fMRI), a device that performs functional near-infrared spectroscopy (fNIRS), a computerized tomography (CT) scanner, and a device the performs nuclear magnetic resonance (NMR).

17. A method, the method using:
    a detection device that detects a brain activity;
    a trigger output device that outputs a first trigger that is a stimulus or a task for a living body, and a second trigger that can change a first brain activity induced by an output of the first trigger,
        wherein, for the first trigger, the stimulus is selected from the group consisting of a visual stimulus and a sound; and
    the method comprising:
    acquiring first brain activity information on the first brain activity;
    acquiring second brain activity information on a second brain activity induced by the output of the first trigger which is accompanied by the output of the second trigger;
    detecting a change in the first brain activity induced by the output of the second trigger based on the first brain activity information and the second brain activity information; and
    selecting a type of inhibitory circuit to be inputted to an excitatory circuit which is to be activated by the first trigger, wherein the inhibitory circuit is selected according to a timing of the output of the second trigger in advance of the output of the first trigger.

18. The method according to claim 17, further comprising selecting a drug candidate that is applied to a subject having a disease related to the inhibitory circuit based on an action of the inhibitory circuit.

19. A method, the method comprising:

acquiring first brain activity information on a first brain activity using the system of claim 1;

acquiring second brain activity information on a second brain activity induced by the output of the first trigger which is accompanied by the output of the second trigger using the system of claim 1;

acquiring a change in the first brain activity induced by the application of the second trigger based on the first brain activity information and the second brain activity information using the system of claim 1;

selecting a type of inhibitory circuit to be inputted to an excitatory circuit which is to be activated by the first trigger, wherein the inhibitory circuit is selected according to a timing of the output of the second trigger in advance of the output of the first trigger; and producing an inhibitory circuit characteristic output capable of being used to produce a product.

* * * * *